US012697057B2

(12) United States Patent
Kermany et al.

(10) Patent No.: US 12,697,057 B2
(45) Date of Patent: Aug. 4, 2026

(54) NEUROMONITORING DATA ANALYSIS APPARATUSES AND METHODS

(71) Applicant: Nervio Ltd., Manof (IL)

(72) Inventors: Einat Kermany, Rakefet (IL); Nir Zarchi, Rakefet (IL); Omer Zarchi, Beit Hashmonai (IL)

(73) Assignee: Nervio Ltd., Manof (IL)

( * ) Notice: Subject to any disclaimer, the term of this patent is extended or adjusted under 35 U.S.C. 154(b) by 280 days.

(21) Appl. No.: 18/403,768

(22) Filed: Jan. 4, 2024

(65) Prior Publication Data

US 2024/0130662 A1 Apr. 25, 2024
US 2024/0225519 A9 Jul. 11, 2024

Related U.S. Application Data

(63) Continuation of application No. PCT/IB2022/056217, filed on Jul. 5, 2022.
(Continued)

(30) Foreign Application Priority Data

Jul. 5, 2021 (IL) .......................................... 284635

(51) Int. Cl.
*A61B 5/388* (2021.01)
*A61B 5/00* (2006.01)

(52) U.S. Cl.
CPC ............ *A61B 5/388* (2021.01); *A61B 5/7264* (2013.01); *A61B 5/7282* (2013.01)

(58) Field of Classification Search
CPC ... A61B 5/389; A61B 2505/05; A61B 5/4893; A61B 5/24; A61B 5/743; A61B 5/377;
(Continued)

(56) References Cited

U.S. PATENT DOCUMENTS 4,705,049 A 11/1987 John
6,306,100 B1 10/2001 Prass
(Continued)

FOREIGN PATENT DOCUMENTS

EP 1719542 11/2006
WO WO 2006/133015 12/2006
(Continued)

OTHER PUBLICATIONS

International Preliminary Report on Patentability Dated Sep. 15, 2015 From the International Bureau of WIPO Re. Application No. PCT/182014/001572. (11 Pages).
(Continued)

*Primary Examiner* — Jon Eric C Morales

(57) ABSTRACT

Aspects of embodiments pertain to systems configured to perform neuromonitoring data analysis, by employing the following: receiving patient data comprising data that are descriptive of at least one physical stimulus applied to a mammalian subject for responsively generating at least one signal in a plurality of neural structures of the subject's nervous system; and sensor data descriptive of at least one neurophysiological response signal generated in response the applied physical stimulus. The systems are further configured to determine, based on the received patient data descriptive of the at least one physical stimulus and the generated response signal, at least one characteristic with respect to at least one of the plurality of neural structures of the patient.

17 Claims, 7 Drawing Sheets

7100 — RECEIVING DATA DESCRIPTIVE OF A PLURALITY OF NEUROPHYSIOLOGICAL RESPONSE SIGNALS GENERATED IN AT LEAST TWO NEURAL STRUCTURES OF A PATIENT AS A RESULT OF SUBJECTING THE PATIENT TO A PLURALITY OF PHYSICAL STIMULI

7200 — IDENTIFYING, BASED ON THE RECEIVED DATA, AN ANOMALOUS EVENT THAT IS INDICATIVE OF INJURY OF AT LEAST ONE OF THE AT LEAST TWO NEURAL STRUCTURES

7300 — PROVIDING A FIRST OUTPUT RELATING TO THE IDENTIFIED EVENT

Related U.S. Application Data

(60) Provisional application No. 63/218,673, filed on Jul. 6, 2021.

(58) Field of Classification Search

CPC ..... A61B 5/388; A61B 5/4821; A61B 5/7264; A61B 17/32; A61B 2562/0219; A61B 5/0006; A61B 5/0036; A61B 5/1104; A61B 5/1107; A61B 5/25; A61B 5/279; A61B 5/296; A61B 5/374; A61B 5/375; A61B 5/383; A61B 5/397; A61B 5/4041; A61B 5/4052; A61B 5/407; A61B 5/4076; A61B 5/4848; A61B 5/6828; A61B 5/6833; A61B 5/6848; A61B 5/704; A61B 5/7217; A61B 5/7267; A61B 5/7282; A61B 5/7405; A61B 5/7425; A61B 5/7445; A61B 5/7455; A61B 5/746; A61N 1/36017; G06F 3/015; G06N 20/20; G06N 3/09; G06N 5/01

See application file for complete search history.

(56) References Cited

U.S. PATENT DOCUMENTS

| | | | |
|---|---|---|---|
| 7,214,197 B2 | 5/2007 | Prass | |
| 7,216,001 B2 | 5/2007 | Hacker et al. | |
| 7,310,546 B2 | 12/2007 | Prass | |
| 8,050,769 B2 | 11/2011 | Gharib et al. | |
| 8,265,744 B2 | 9/2012 | Gharib et al. | |
| 8,323,208 B2 | 12/2012 | Davis et al. | |
| 8,500,653 B2 | 8/2013 | Farquhar | |
| 8,568,317 B1 | 10/2013 | Gharib et al. | |
| 8,989,855 B2 | 3/2015 | Murphy et al. | |
| 9,211,074 B2 | 12/2015 | Johnson et al. | |
| 9,295,401 B2 | 3/2016 | Cadwell | |
| 9,566,015 B2 | 2/2017 | Murphy et al. | |
| 9,655,505 B1 | 5/2017 | Gharib et al. | |
| 9,700,228 B2 | 7/2017 | Gharib et al. | |
| 9,757,067 B1 | 9/2017 | Gharib et al. | |
| 9,757,072 B1 | 9/2017 | Urbalejo | |
| 9,949,651 B2 | 4/2018 | Stone et al. | |
| 10,022,090 B2 | 7/2018 | Whitman | |
| 10,039,461 B2 | 8/2018 | Cadwell | |
| 10,098,585 B2 | 10/2018 | Scott et al. | |
| 2006/0276720 A1 | 12/2006 | McGinnis et al. | |
| 2009/0048531 A1 | 2/2009 | McGinnis et al. | |
| 2010/0145222 A1 | 6/2010 | Brunnett et al. | |
| 2010/0312124 A1 | 12/2010 | Johnson et al. | |
| 2011/0230785 A1 | 9/2011 | Higgins et al. | |
| 2012/0095360 A1 | 4/2012 | Runney et al. | |
| 2014/0051999 A1 | 2/2014 | Gharib et al. | |
| 2015/0032022 A1 | 1/2015 | Stone et al. | |
| 2015/0230749 A1 | 8/2015 | Gharib et al. | |
| 2015/0238259 A1 | 8/2015 | Albeck et al. | |
| 2016/0270679 A1 | 9/2016 | Mahon et al. | |
| 2017/0348052 A1 | 12/2017 | Albeck et al. | |
| 2018/0256051 A1 | 9/2018 | Stone et al. | |
| 2019/0038169 A1 | 2/2019 | Lekenga et al. | |
| 2019/0076088 A1 | 3/2019 | Whitman | |
| 2020/0315478 A1 | 10/2020 | Mahon et al. | |
| 2020/0352468 A1 | 11/2020 | Runey et al. | |
| 2021/0093228 A1 | 4/2021 | Wybo et al. | |

FOREIGN PATENT DOCUMENTS

| | | |
|---|---|---|
| WO | WO 2019/207510 | 10/2019 |
| WO | WO 2023/281399 | 1/2023 |

OTHER PUBLICATIONS

International Search Report and the Written Opinion Dated Dec. 12, 2022 From the International Searching Authority Re. Application No. PCT/IB2022/056217. (17 Pages).

Lee "Clinical Applications of Continual Learning Machine Learning", The Lancet, Digital Health, 2(6): e279-e281, Jun. 2020.

Qiao et al. "Deep Learning for Automatically Visual Evoked Potential Classification During Surgical Decompression of Sellar Region Tumors", Translational Vision Science & Technology, 8(6), Art.21: 7P., Nov. 2019.

Zha et al. "A Deep Learning Model for Automated Classification of Intraoperative Continuous EMG", IEEE Transactions on Medical Robotics and Bionics, 3(1):44-52, Dec. 30, 2020.

Supplementary European Search Report and the European Search Opinion Dated Oct. 25, 2024 From the European Patent Office Re. Application No. 22837133.2. (11 Pages).

Fan et al. "An Intelligent Decision System for Intraoperative Somatosensory Evoked Potential Monitoring", IEEE Transactions on Neural Systems and Rehabilitation Engineering, XP011599871, 24(2): 300-307, Published Online Sep. 23, 2015.

Lieberman et al. "The Reliability of Motor Evoked Potentials to Predict Dorsiflexion Injuries Lumbosacral Deformity Surgery: Importance of Multiple Myotomal Monitoring", The Spine Journal, XP085598874, 19(3): 377-385, Published Online Jul. 17, 2018.

Zhang et al. "A Survey on Deep Learning Baised Brain Computer Interface: Recent Advances and New Frontiers", ArXiv Preprint ArXiv:1905.04149v1, XP081370914, 67 P., May 10, 2019.

International Preliminary Report on Patentability Dated Jan. 18, 2024 From the International Bureau of WIPO Re. Application No. PCT/IB2022/056217 (12 Pages).

Response To Section 18 Notification Jul. 20, 2021 Re. Application No. 284635. (3 Pages).

Search Report Dated Oct. 18, 2021 From the Israel Patent Office Re. Application No. 284635. (6 Pages).

Nim Eclipse E4 "NIM-ECLIPSE® E4 Nerve Monitoring System", Product Description, Medtronics: 4P., 2015.

Nim-Eclipse "NIM-Eclipse® SD Surgeon Directed NIOM", User's Manual, Software Version 3.5.350: 154P., Dec. 2010.

Communication Pursuant to Article 94(3) EPC Dated Nov. 18, 2025 From the European Patent Office Re. Application No. 22837133.2 (9 Pages).

Charalampidis et al. "The Use of Intraoperative Neurophysiological Monitoring in Spine Surgery", Global Spine Journal, XP093334110, 10(15): 1045-1145, Jan. 1, 2020.

Wang ct al. "Component Analysis of Somatosensory Evoked Potentials for Identifying Spinal Cord Injury Location", Scientific Reports, XP093333934, 7(1):2351-1-2351-12, May 24, 2017.

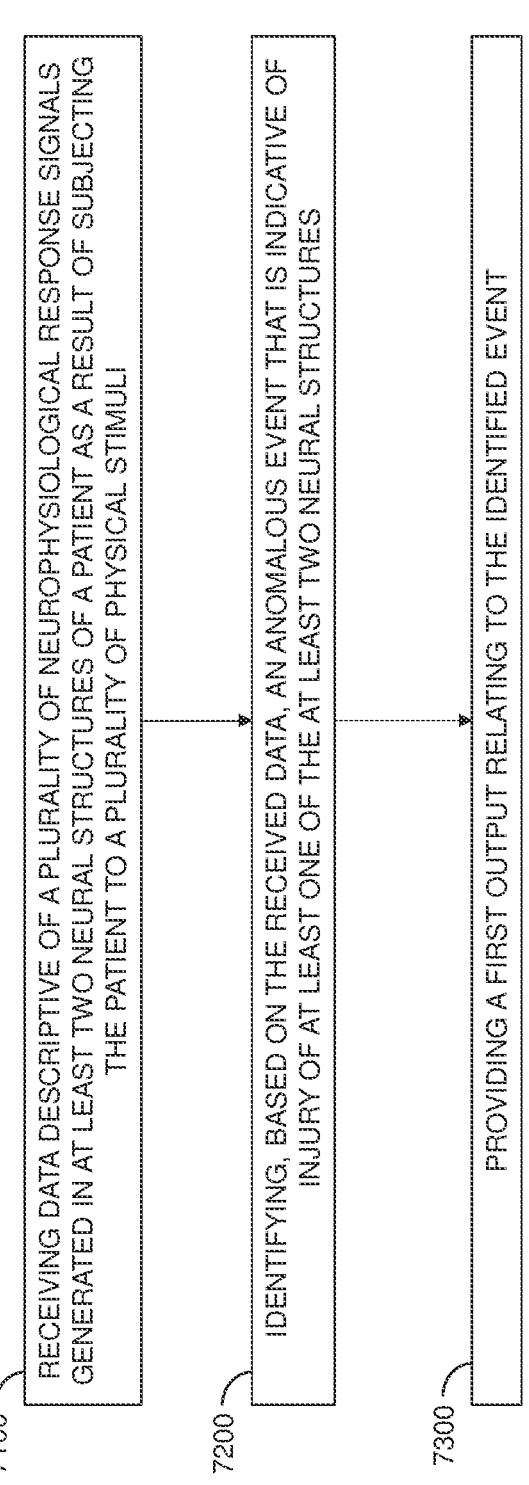

7100 RECEIVING DATA DESCRIPTIVE OF A PLURALITY OF NEUROPHYSIOLOGICAL RESPONSE SIGNALS GENERATED IN AT LEAST TWO NEURAL STRUCTURES OF A PATIENT AS A RESULT OF SUBJECTING THE PATIENT TO A PLURALITY OF PHYSICAL STIMULI

7200 IDENTIFYING, BASED ON THE RECEIVED DATA, AN ANOMALOUS EVENT THAT IS INDICATIVE OF INJURY OF AT LEAST ONE OF THE AT LEAST TWO NEURAL STRUCTURES

7300 PROVIDING A FIRST OUTPUT RELATING TO THE IDENTIFIED EVENT

FIG. 7

NEUROMONITORING DATA ANALYSIS APPARATUSES AND METHODS

RELATED APPLICATIONS

This application is a Continuation of PCT Patent Application No. PCT/IB2022/056217 having International filing date of Jul. 5, 2022, which claims the benefit of priority under 35 USC § 119(e) of U.S. Provisional Patent Application No. 63/218,673 filed on Jul. 6, 2021 and of Israeli Patent Application No. 284635 filed on Jul. 5, 2021. The contents of the above applications are all incorporated by reference as if fully set forth herein in their entirety.

BACKGROUND

The present disclosure relates in general to neuromonitoring including, for example, intraoperative neuromonitoring. Intraoperative neuromonitoring is essential to avoid or reduce the risk of causing inadvertent damage to a patient's neural structures when performing surgical procedures in tissue regions such as the spine or brain. During surgery, neurologists with expertise in intraoperative neurological monitoring (IONM) analyze the recordings of neurological signals to provide early warning to the surgeon to prevent or mitigate functional neural deficit.

The description above is presented as a general overview of related art in this field and should not be construed as an admission that any of the information it contains constitutes prior art against the present patent application.

BRIEF DESCRIPTION OF THE FIGURES

The figures illustrate generally, by way of example, but not by way of limitation, various embodiments discussed in the present document.

For simplicity and clarity of illustration, elements shown in the figures have not necessarily been drawn to scale. For example, the dimensions of some of the elements may be exaggerated relative to other elements for clarity of presentation. Furthermore, reference numerals may be repeated among the figures to indicate corresponding or analogous elements. References to previously presented elements are implied without necessarily further citing the drawing or description in which they appear. The figures are listed below.

FIG. 7 is a flowchart of a method for monitoring a nervous system of a patient, according to some embodiments.

DETAILED DESCRIPTION

Figure 1:
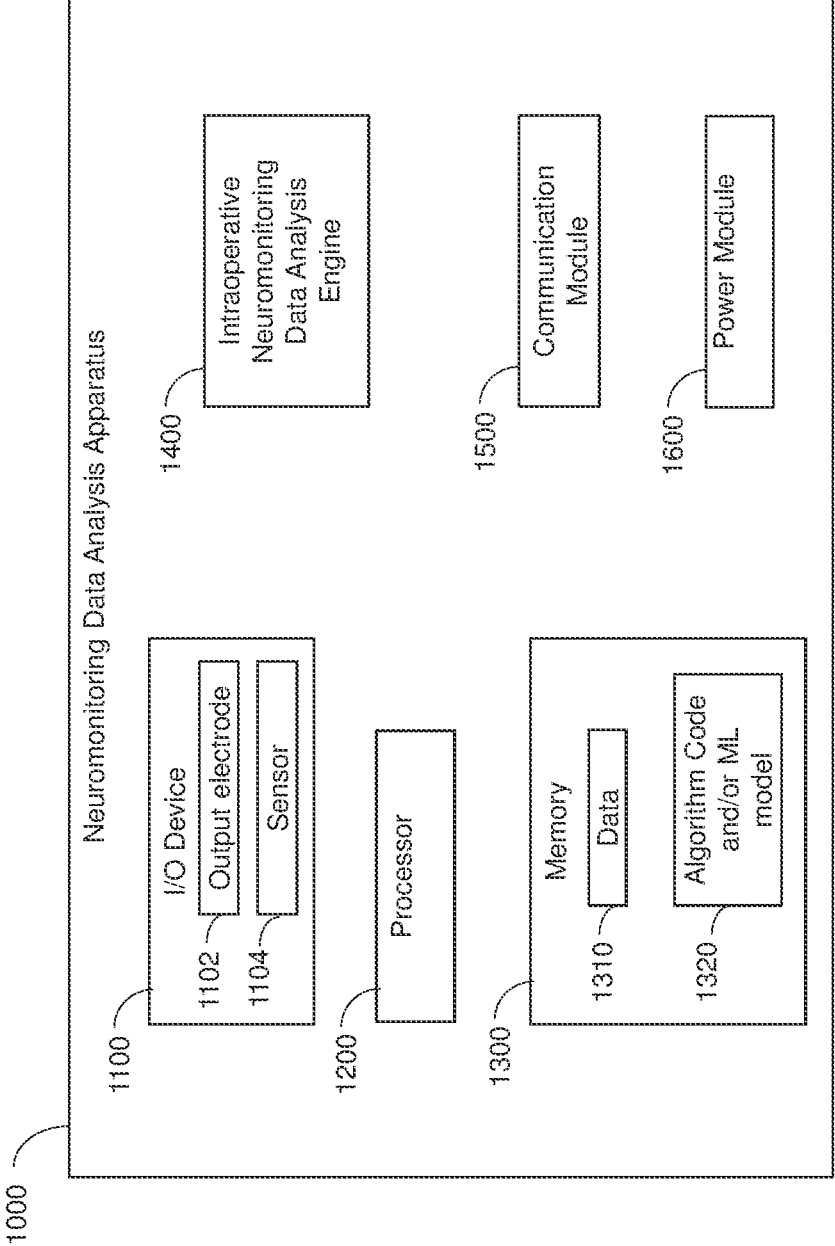
FIG. 1 shows a schematic block diagram illustration of a neuromonitoring data analysis apparatus, according to some embodiments.

Aspects of disclosed embodiments pertain to automated or semi-automated neuromonitoring based on patient data relating to sensed and/or measured neurological signals received (directly and/or indirectly) and processed by a neuromonitoring data analysis apparatus. In some embodiments, the apparatus is operable and/or configured to provide an output relating and/or descriptive of a patient's current functional neural state, optionally along with a clinical interpretation thereof. In addition, the neuromonitoring data analysis apparatus may be operable and/or configured to perform functional mapping of neural structures, regions, nerves and/or nerve roots, for example, in the spinal chord and brain region. Moreover, in some embodiments, the neuromonitoring data apparatus may be configured to determine a functional state of reflectory reactions or reflexes in response to a (neural) stimulus. In some examples, an output relating to the data analysis performed by the apparatus may be provided (e.g., displayed visually and/or audibly), by an output device of a neuromonitoring system employed for (e.g., intraoperatively) monitoring the nervous system of a patient undergoing a medical (e.g., surgical) procedure, and/or by the analyzing apparatus, which analyzes data received, inter alia, from the intraoperative neuromonitoring system. Hence, although embodiments may for example describe the providing of nervous system monitoring information by the monitoring system and the providing of related analysis output by the analysis apparatus, this should by no means be construed in a limiting manner. For example, an analysis output (e.g., alert, flag) produced by the apparatus may be displayed in overlay with nervous system monitoring information (e.g., signal plots) displayed by the monitoring system. In some examples, the analysis apparatus may not provide an output but merely perform the analysis to produce an analysis result (e.g., anomaly classification).

Some of the patient data may include pre-operatively received patient data, and some of the patient data may include intraoperatively received patient data.

Patient data may relate to a patient's neurological functionality and for example be descriptive of at least one physical (e.g., neural) stimulus applied to a mammalian subject (e.g., a human subject) for responsively generating at least one signal in a plurality of neural structures of the patient's nervous system. The patient data may further be descriptive of sensor data descriptive of at least one response signal generated in response to the applied one more physical stimuli.

In some embodiments, the patient data may be descriptive of anatomical (e.g., structural) patient information and/or physiological patient information, in addition to information of the patient's neurological functionality. Additional physiological patient information may for instance also include the patient's temperature, weight, blood oxygen saturation, electrocardiography information, and/or the like.

The neuromonitoring data analysis apparatus may be configured to determine, based on the received patient data, at least one characteristic with respect to at least one of the plurality of neural structures. The characteristic may pertain to a neural functional state which may for instance be indicative of an anomaly (e.g., deficit) in the functionality of a neural structure of the patient. In some examples, an output relating to a characteristic of a functional state may include an alert, e.g., when the deficit meets an alert output criterion, e.g., if one or more conditions are met for outputting an alert. In some examples, the alert output criterion may be met if the apparatus identifies that a severity of a deficit exceeds a severity threshold. In some examples, the alert output criterion may be met if the apparatus identifies that the surgically induced deficit may possibly cause an irreparable deficit (e.g., permanently harm or injure the neural structure) or an irreparable deficit exceeding a certain severity or a reparable deficit (e.g., allowing recovery of the neural structure) exceeding a certain severity. The apparatus is operable to distinguish between neural signal anomalies clinically significant with respect or as clinically related to injury of neural structures (e.g., indicative of injury caused to neural structure), which may be caused by surgical accessories or instruments employed for engaging with tissue near or adjacent neural structures, and neural signal anomalies which are not related to injury of neural structures (e.g., classify these anomalies as clinically unrelated to injury of neural structures). The alert may include information about a specific clinical condition of the patient with respect to intraoperatively monitored neural parameter values. For example, the apparatus may be configured to provide a clinical interpretation of the patient data including, for example, a type of neural pathway that is injured (also: insulted, a severity of the injury (also: insult) and/or resulting deficit, along with the location and/or region of origin of the neural injury, along with the location and/or region of the resulting functional deficit. In some embodiments, the apparatus may be configured to identify a misconfiguration of a neuromonitoring system or setup and alert a user that a detected anomaly (also: anomalous parameter value) is due to such misconfiguration. For example, the apparatus may alert the user about a wrong or inadequate engagement of the sensing and/or stimulus electrodes with the patient.

It is noted that, in some examples, the expression "injury of a neural structure", "neural injury", and/or "functional deficit" as used herein (as well as grammatical variations thereof), may relate to situations where integrity of the neural structure is adversely affected as a result of direct surgical engagement with the corresponding neural structure. In some examples, the apparatus may be configured to distinguish between "cord injury", "nerve injury" and optionally provide corresponding outputs.

It is further noted that the expression "injury" with respect to neural structure due to surgical engagement may pertain to non-permanent and/or permanent injury. The neural structure may at least partially or fully recover following the injury, for example, as a result of the data analysis apparatus alerting a medical professional (e.g., surgeon, or neurologist) when surgical accessory employed by the surgeon is, for example, an acceptable distance away from the neural structure where injury may be reparable and/or within a non-acceptable distance away from the neural structure, potentially causing irreparable harm or injury to the neural structure.

The neuromonitoring system may be configured to monitor spontaneous and non-spontaneously generated neurophysiological signals. For instance, the system may be configured to intraoperatively apply at least one physical (e.g., electrical, auditory, and/or visual) stimulus to the patient (also: target individual or mammalian subject) relating to at least one neural signal measurement modality to generate and/or monitor measurable neural activity signals in neural structures of the patient's nervous system.

The at least one neural measurement modality may pertain to the monitoring of, for example, to motor evoked potential (MEP) signals, somatosensory evoked potential (SSEP) signals, reflexes (e.g., H-reflex, bulbocavernosus reflex, blink reflex), autonomous neural signals (ANS), electromyography (EMG) signals, Electroencephalography (EEG) signals and/or other neural signals.

For example, during brain surgery, a suction device applies electrical stimulation to determine how close the suction device is to the motoric pathways including the corticobulbar tract by measuring the corresponding muscle response.

The apparatus is further configured to analyze and/or process data relating to the neural signals obtained by the at least two different neural signal measurement modalities to determine the patient's (e.g., present) functional neural state, for example, by comparing a plurality of present neural signals against a plurality of normal baseline values of the individual's neural functional signals (e.g., in a situation where the patient does not undergo a surgery procedure). In some examples, a neural state may be expressed in functional staging parameter values.

In some embodiments, the apparatus may be configured to process and analyze the various neurological stimulus and response signals and, optionally, process and analyze additional patient data (e.g., pre-operative and intraoperatively received physiological parameter values) received at the neuromonitoring data analysis apparatus, to yield an analysis result for presentation to a user. In some embodiments, the analysis output may indicate whether neurological functions are normal or not. For instance, the apparatus may be configured to classify a functionality of a neural structure as normal or anomalous. In some embodiments, the apparatus may be configured to determine whether an anomalous parameter value falls into one of the following two or more categories: a first anomaly that is indicative of a functional deficit and/or injury of the neural structure, and a second anomaly that is not indicative of or does not relate to a functional deficit and/or injury of the neural structure.

In some embodiments, as briefly mentioned above, the apparatus may be configured to output, based on input data, a clinical interpretation of the monitored neurological signals.

The apparatus may provide and/or change a present output displayed by the system based on the performed analysis. The analysis may include determining whether a criterion is met to display or update a system output relating to target individual's neural functional state and/or change thereof. In some embodiments, the analysis may be provided automatically without the user's intervention.

In some embodiments, the user may provide the apparatus with command input to perform a selected analysis. In some embodiments, the neuromonitoring data analysis apparatus may be configured to intraoperatively present the user with a list of possible command inputs relating to intraoperative neuromonitoring and functional assessment. For example, the user may enter (e.g., via an I/O of the system and/or the apparatus) a type of surgery, age patient, spine, brain, and/or leads to different intraoperative neuromonitoring protocols. Moreover, the surgeon provides input regarding different steps in surgery, based on which the apparatus applies different protocols. For example, motoric stimulation from/ transcranial motor evoked potential for instance must be performed only when surgeon gives approval.

In some embodiments, the apparatus may be configured to automatically apply a sequence of checks. For instance, the apparatus may apply a number of tests to be performed by the system to check or analyze motor function by the apparatus. If the outcome of the tests indicates a deficiency in the motoric function then the apparatus may analyze the situation, provide one or more outputs indicating the reasons why the tests yielded results indicative of a deficient motor function, and optionally, provide recommendations with respect to performing additional tests including, for example, increase stimulation. In some examples, the apparatus may autonomously or semi-autonomously (e.g., subject to surgeon's approval), cause a neuromonitoring system to apply additional stimulation(s).

In some embodiments, the apparatus may automatically, autonomously and continuously determine which analysis output is to be displayed to the user (e.g., via a display of the system), depending on the present situation, and to provide recommendations regarding additional stimulations to be performed and their related parameter values.

In some embodiments, the analysis may be performed by way of one or more machine learning models or algorithms, such as artificial neural networks (ANNs), to provide an output indicative of the patient's functional neural state. In some embodiments, the apparatus may be configured to perform signal analysis using heuristics models. Further, in some instances, the machine learning and heuristics models may be combined into a hybrid model for performing neuromonitoring signal analysis.

In some embodiments, the machine learning model may be trained based on a plurality of analyses previously performed by a professional in the field of neuromonitoring. In some examples, the apparatus may be configured to receive data descriptive of neuromonitoring analysis information which may be used as input training data for the AI-based machine learning model. In some embodiments, the analysis information may be provided intraoperatively.

The dataset for training the machine learning model may be segmented as follows:

60% training data based on which the ML model is trained;

20% test data based on which the ML is not trained; and

20% validation data, which is used to validate parameter values, for instance, to prevent overfitting. The datasets may be separated randomly.

In some embodiments, the machine learning model may be updated intraoperatively by labelling, in under real-life conditions, data related to intraoperative neuromonitoring. In some embodiments, data associated with previously performed neuromonitoring analysis may be "mined" or otherwise processed to extract rules and observations that may be used in the process for future neuromonitoring analyses and/or as training input data for training a neuromonitoring machine learning model. In some embodiments, the machine learning model may comprise a classifier. In some examples, the classifier may be a regression-based classifier, based on artificial neural networks (ANNs) or based on Gradient Boosting model.

The Gradient Boosting algorithm produces a prediction model that is based on an ensemble of weak prediction models (e.g., decision trees). The model is designed to solve an optimization problem that tries to minimize the difference between the model predictions on a test dataset, and the real labels on a dataset of labelled data. In some examples, real labels may be provided by an expert on-the fly in an online or real-life scenario, e.g., as outlined herein.

In some examples, the machine learning model may be considered by evaluating labels produced by a test dataset. The validation measures may include, for example, accuracy, recall and/or precision, with respect to real labels on a dataset of labeled data.

In some embodiments, an output indicative of target individual's neural functional state and/or change thereof may be provided (e.g., displayed), for example, in the form of categorical, ordinal and/or numerical parameter values. A neural functional state output may indicate whether a functional state is normal, deficient, about to become deficient, improving or about to improve. The function of a neural structure may become deficient or otherwise altered due to insult and/or due to systemic factors (including, e.g., anesthesia agents, blood pressure, body temperature). For example, the system may be configured to identify and alert the user of systemic physiological state such as hypotension, and further configured to determine if the detected hypotension is a result of deep anesthesia, hypothermia, and/or the result of a technical problem.

In some embodiments, the neuromonitoring data analysis apparatus may be configured to distinguish between changes indicative of neurological changes (e.g., indications relating to neurological deficiency) which are the result of neurological injury, changes which are the result of systemic factors and/or due to neuromonitoring system malfunction and/or misconfigurations.

In some examples, the neuromonitoring data analysis apparatus may identify systemic-related signal contribution or fluctuations, offset systemic-related signal contribution/fluctuations from the total signal to analyze whether a change in neural function is also or solely due to systemic factors or not. In some examples, the neuromonitoring data analysis apparatus may be configured to output a warning about signal artifacts introduced due to systemic physiological conditions and/or environmental conditions (electrical artifacts and electromagnetic noise), which can impair the reliability of neurophysiological monitoring.

Injury of neural structures may cause neural functional anomaly such as partial deficit or complete functional disablement. Moreover, injury may cause permanent or non-permanent functional deficit. Neural structure functionality may be non-reversible, partially reversible, or fully reversible.

The apparatus may be configured to provide the output in real-time. It is noted that the expression "real-time" may also encompass the meaning of the term "near real-time". The expression "real-time" as used herein generally refers to the updating of information at essentially the same rate as the data is received. In the context of the present disclosure, "real-time" is intended to mean that neurophysiological signals are recorded and processed (e.g., analyzed), at a high enough data rate and at a low enough time delay that the output is displayed without user-noticeable judder, latency or lag.

In some embodiments, an apparatus' output of a neural functional state for example may be indicative of a "normal" functional state, or of an anomaly such as, for example, a "deterioration" or "drop" from a normal and/or current functional state, an impending "deterioration" or "drop" from a normal and/or current functional state to a low functional state, and/or indicate a present or impending "disappearance" of a normal or low functional state, as determined with respect to a plurality of normal baseline values of the neural functional signals. Clearly, additional or alternative labels may be output by the apparatus.

Neural functional anomaly (e.g., drop from a normal functional state, increased latency, etc.) may manifest itself in several ways. Considering for example, an evoked potential signal (MEP and/or SSEP) and a baseline response signal, a signal characteristics (e.g., relating to amplitude, frequency, and/or phase) of a response signal may be categorized as follows: no response, remnant of response, significant drop from baseline response, moderate drop from baseline response, normal, increased response to baseline response, increased latency, and/or the like. In some examples, a detected anomaly in MEP and/or SSEP response signals may be identified by the apparatus as the result of a technical problem. For example, with respect to SEP signals and/or EEG we perform bandpass filtering is may be performed because comparatively low frequency components introduce bias which may distort the analysis of the signals.

With respect to EEG signals, in some embodiments, the neuromonitoring data analysis apparatus may be configured to analyze EEG signal characteristics in the spectral and time domains, and, for example, perform signal power analysis. Signals characteristics may be used as indicators of cortical functional state and of its arousal. In some examples, the EEG analysis may detect systemic physiological states which are inadequate for reliable neuromonitoring. In some examples, the EEG analysis can help assess the extent of which fluctuations in monitored signals, e.g., MEP, SSEP and various reflexes, are due to the influence of systemic factors.

In some embodiments, the neuromonitoring data analysis apparatus may be configured to process EMG signals. With respect to EMG signals, an anomaly (e.g., a deviation from "quiet") may for example be characterized by train signals and/or bursts. In some examples, an anomaly detected in EMG signals may be identified by the apparatus as the result of a technical problem or from a low level of anesthesia.

In some embodiments, an apparatus' output of a neural functional state for example may be indicative of an "improvement" with respect to a pre-existing functional state, an impending "improvement" from a pre-existing functional state, and/or indicate a present or impending "reappearance" or "reinstatement" of a previously disappeared normal or low functional state.

In some embodiments, a neural functional state may indicate a degree of severity of a current deficit of a functional state, a likelihood or probability of a present situation to cause a functional deficit in the nervous system of a certain severity and/or the like, in the target individual, for instance, within a certain period of time. In some embodiments, a neural functional state may indicate a degree of adequacy of a neural functional state, a likelihood or probability of a present situation to increase the adequacy of a present functional neural state, and/or the like.

In some embodiments, the apparatus may provide an output indicating when a neural functional state is deficient due to improper neuromonitoring system setup or not. For example, the apparatus is configured to distinguish between baseline and response signals and further configured to indicate whether differences in baseline and response signals discrepancies are a result of technical problems, wrong neuromonitoring system setup, and/or due to surgery-induced physiological neural functional deficiencies.

In some embodiments, the neuromonitoring data analysis apparatus may be configured to provide an output including a clinical interpretation of the received patient data. In some examples, to provide a clinical interpretation, functional neural states and related outputs may be time-stamped and recorded along with an indication of the one or more actions performed on the target individual. For example, a neurophysiologist's actions for conducting intraoperative neuromonitoring (IONM) along with a surgeon's actions and/or an anesthetist's actions performed on the patient and/or the patient's position may be continuously monitored (e.g., sensed and recorded along with a time stamp) and considered by the apparatus for providing an analysis output. For example, positions and duration where a surgeon operably engages with the target individual or patient may be continuously recorded, analyzed and, optionally output (e.g., displayed) by the apparatus.

In some embodiments, the apparatus may be configured to determine (e.g., classify) a neural functional state (e.g., "normal" or "deficient") in association with the type of neural structure (e.g., pathway). For example, the apparatus may be configured identify and present that an anomaly is associated with motor neural pathway, sensory neural pathway and/or an autonomous neural pathway; along with the anatomical location or region.

In some embodiments, neuromonitoring data analysis apparatus may not only be configured and operable to determine a functional neural state, but also perform mapping of nerves and nerve roots. In some examples, the neural mapping may be associated with a determination of a functional neural state.

For example, an anatomical location or region (and, e.g., an associated deficient somatosensory function) may be identified, for example, as left side, right side; bilateral; high cervical (e.g., neck vertebrae), low cervical (e.g., lumbar spine), thoracic; (right and/or left) upper and/or lower extremity, lower extremity), along with an associated functional state (no deficit, partial deficit, complete deficit); and/or the like.

In some embodiments, the apparatus may determine and, optionally, providing an indication that no specific location can be associated with a particular functional state.

In some embodiments, the apparatus may be configured to map the determined a neural structure. Mapping of nerves and nerve roots may be performed by the apparatus through triggered EMG. For example, in triggered EMG, a nerve and, optionally, its functional state, may be associated with myotome including, for example, L-Deltoid, L-Biceps, L-Triceps, L-Thenars, R-Deltoid, R-Biceps, R-Triceps, R-Thenars, or any combination of the above. Mapping-related information may for example be presented to a user by an I/O device of the system and/or of the apparatus.

In some embodiments, the neuromonitoring data analysis apparatus may be operative to map brain regions brain mapping may be performed by the neuromonitoring data analysis apparatus through direct brain stimulation. The neuromonitoring data analysis apparatus may further provide an output indicative of the state of the specific neurological function of the localized nerve or nerve root.

Both triggered EMG and direct brain stimulation are performed with the help of electrical stimuli with different or distinct characteristics that are submitted through a probe or through the surgical tool.

In one example scenario, a brain region that is operably engaged by the surgeon may be mapped automatically with respect to a certain nerve root, and presented to the user (e.g., by the system and/or by the apparatus) along with a corresponding functional label and functional state.

For example, nerve root mapping in infratentorial brain pathways such as Cauda Equina during tumor removal surgery can be performed using probe stimulation and triggered EMG recording. The neuromonitoring data analysis apparatus analyzes the stimulus responses from the corresponding muscles and the stimulus thresholds that trigger the response, and warns of proximity to a nerve root in the brain.

In a further example, continuous motor mapping of the cortex and subcutaneous white matter (supratentorial brain pathways) can be performed by probe stimulation or by continuous stimulation delivered through the section. The apparatus analyzes the stimulus responses and the stimulus thresholds that trigger the response, and warns of proximity to a motor area in the surgical field.

Analogously, with respect to spine surgeries, the apparatus may be configured to automatically identify the type of neural pathway (e.g., somatosensory, motor sensory or autonomous neural signals, or any combination of the aforesaid) that is operably engaged by the surgeon during surgery, along with an output indicating the location (e.g., relative to vertebrae position) where the surgeon engages a spinal nerve.

In some embodiments, the neuromonitoring data analysis apparatus may be configured to determine a functional state of a reflex arc by sensing characteristics related to reflectory reactions or reflexes in response to a stimulus. Example reflexes can include, for example, the H-reflex during thoracic spine surgery, the bulbocavernosus reflex, the blink reflex and/or the like.

In some embodiments, the apparatus may be configured to provide an output indicative of actionable instructions on how to maintain a present (e.g., normal) neural functional state, taking possible steps in order to reverse deterioration in neurological function or to prevent further deterioration.

Actionable instructions may include, for example, one or more follow-up tests and/or adaptation of parameter values, to improve or optimize, for example, a patient's physiological systemic state for neurophysiological monitoring.

In some embodiments, the output may pertain to instructions for validating a system output.

In some embodiments, the neuromonitoring data analysis apparatus may be configured to provide decision support when an anomaly is detected and identified (e.g., classified). For example, the apparatus may provide the user with an output indicative of actionable suggestion or instructions to the user on how to validate, overcome, or rectify the anomaly to revert to a normal functional state. For example, the neural monitoring apparatus output may include instructions or suggestions to evoke additional motor evoked potential; instructions or suggestions to evoke additional somatosensory evoked potential; instructions or suggestions to change stimulus-related characteristics (e.g., intensity, polarity) of the additional motor evoked potential; instructions or suggestions to change stimulus intensity of the additional somatosensory evoked potential, reflex stimulus, and peripheral nerve stimulation such as train-of-four (TOF), and/or the like.

In some embodiments, the output may include instructions or suggestions to update and/or alter recording parameters; instructions or suggestions pertaining to neuromonitoring system malfunction identification checks and/or configuration checks; instructions or suggestions how to overcome system malfunction and/or misconfiguration, including instructions or suggestions for automated, semi-automated and/or manual troubleshooting neuromonitoring system misconfiguration. The output can include, for example, (e.g., troubleshooting) instructions or suggestions such as updating recording parameters; system malfunction checks; impedance check; anesthesia parameter checks; electrode contact checks; instructions to check physiological patient parameters; instructions or suggestions to check patient position; instructions or suggestions to put the surgical procedure on hold; or any combination of the aforesaid. In some scenarios, the output provided by apparatus may indicate the user to not undertake any additional steps.

A user of the neuromonitoring data analysis apparatus may provide the apparatus and/or the neuromonitoring system with command inputs, for example, in accordance with the received system outputs, and as mentioned above, in a real-life scenario setting, information about the surgical phase.

In some embodiments, an output relating (e.g., descriptive) of a neural functional state may be provided in conjunction with an output descriptive of a structural state, for example, via medical imagery obtained through one or more imaging modalities including, for example, X-ray (including, e.g., computer-tomography) based imaging technique, nuclear imaging techniques, MRI imaging techniques and/or ultrasound imaging techniques.

In some embodiments, the neuromonitoring data analysis apparatus is configured (e.g., provide a human-machine interface) to enable training a machine learning mode through offline labelling of neurological data which were recorded during a surgical procedure performed and completed in the past. Offline labelling is performed under conditions that try to imitate real-life clinical conditions, e.g., retrospectively.

In some embodiments, a labelling platform is provided that is configured to enable, offline (e.g., retrospective) labelling of various neurophysiological data, and/or online or "real-time" labeling during a simulated or real surgical procedure for training purposes of a machine learning model.

In some embodiments, the labelling platform may be configured as an add-on module of a neuromonitoring system employed for receiving and recording patient data. In some examples, the neuromonitoring data analysis apparatus may be comprised in the neuromonitoring system. In some embodiments, a subsystem may comprise both a neuromonitoring data analysis apparatus and a labelling platform. In some examples, a neuromonitoring data analysis apparatus may comprise a labelling platform. In some further examples, a labelling platform may comprise a neuromonitoring data analysis apparatus. Merely to simplify the discussion that follows, without be construed in a limiting manner, the neuromonitoring data analysis apparatus and the labelling platform are herein referred to as separate entities.

Online or "real-time" labelling of various neurophysiological data with respect to clinical events in a real-life scenario setting enables performing a real-time investigation of a situation during surgery, (e.g., by taking into consideration environmental parameters such as noises or sounds made by equipment, questioning of the surgeon, questioning of the anesthetist, giving instructions to the surgeon and/or the anesthetist), to arrive at corresponding labelling of neurophysiological data received by the apparatus. The labelling platform may thus enable "open" machine learning such that the machine learning model can be continuously adapted. By contrast, in a closed machine learning process, the machine learning model is fixed and does not change during employment of the neuromonitoring data analysis apparatus. In some embodiments, the machine learning model of the neuromonitoring data analysis apparatus may be updated "on-the-fly" by employing the online labelling platform disclosed herein.

In some examples, labels provided online may be compared against output labels generated by the apparatus in a retrospective setting or offline scenario.

Training a machine learning model in an online setting (e.g., intraoperatively) may lead to different and more realistic labelling of neurophysiological data and, thus, to better training of the model, than in offline labelling settings, as exemplified herein.

Example 1 Relating to Online Labelling Vs Offline-Labelling

In one example scenario, minutes after the induction of anesthesia and completion of the neurophysiological setup for a cervical decompressive surgery, the surgeons position the patient. At these moments marked deterioration in the neurophysiological signals is recorded.

The neurophysiologist (or "expert") may be required to distinguish between two events that may be responsible for this deterioration:

Labelling Option 1A: A benign systemic effect as a result of changes made by the anesthesiologist in the dosage of the anesthesia agents to establish a proper depth of anesthesia.

Labelling Option 1B: An evolving cord injury as a result of increased pressure under which the spinal cord is placed at the new head position.

To arrive at a decision which of the two events is applicable, the neurophysiologist can, in the online labelling scenario, question the anesthetist to inquire what he did in the past minutes to determine whether neurophysiological deterioration occurred due to deepening of the anesthesia, or not. In the latter case, the increased neurological deficit is more likely due to pressure to which the spinal cord is subjected, than due to increased depth of the anesthesia.

Clearly, in an offline labelling setting, questioning the anesthetist is not possible and the labelling relating to the observed deterioration of the neurophysiological signal is performed by "guessing" the most likely scenario, for example, by moving forward and backward in time along the length of neurophysiological data recorded in the past for corresponding or similar surgical procedure, to imitate a real-life scenario. However, such "guessed" or retrospective labelling may of course not reflect the actual clinical situation present when the surgical procedure was performed, possibly giving rise to incorrect labelling and, therefore, to suboptimal or incorrect training of the machine learning model. By contrast, online labelling settings reflect more accurately the given actual clinical situation. Thus, online labelling is more likely less prone to bias and errors.

Example 2 Relating to Online Labelling Vs Offline-Labelling

In a further example, online labelling allows performing follow-up tests and change test parameters to confirm or refute hypotheses. By contrast, when performing offline labelling, the testing of hypotheses is not possible.

In relation to Example 1, the neurophysiologist may recommend the operating room staff to reduce the depth of anesthesia, and, if no neurological improvement is evident, to change the patient's position. In this way, it will be possible to reliably distinguish between the two (e.g., possible or probable) causes of decreased neurophysiological function.

Additional steps that the neurophysiologist performs as part of the situation include:

Option 2A: technical tests of the neuromonitoring system and setup to rule out technical failures, Option 2B: increasing the intensity of the stimulus or changing polarity or location of the stimulus, Option 2C: increasing the frequency of tests to assess the trend over few minutes.

All the above-noted options will allow the neurophysiologist to arrive at a more accurate diagnosis, thus leading to both better treatment and more accurate labeling.

Example 3—Improving or Optimizing a Testing Set for the Validation of the Algorithm/Machine-Learning Model In order to objectively examine performance of a neuromonitoring data analysis apparatus, it may be necessary to monitor a surgical procedure in a situation in which the neurophysiologist uses a labelling platform to label, during the (real or simulated) surgery, monitored data under real-life conditions, in real-time, or substantially in real-time. This way, the labeling input provided reflects the neurophysiologist's performance authentically when all the information available in the operating room is at his disposal, and without him being able to know how the surgery will develop in the future.

At the same time, a neuromonitoring data analysis apparatus receives patient data of the same surgical procedure and outputs labels according to the algorithm and/or trained machine learning model, independent of the labelling provided to the labelling platform. The labels which are output by the neuromonitoring data analysis system can be compared against the labels provided by the physician to the labelling platform. This allows comparing the physician's labels against the labels which are output by the neuromonitoring data analysis apparatus. The comparison allows analyzing the performance of the neuromonitoring data analysis apparatus in a reliable manner.

In some embodiments, the neuromonitoring data analysis apparatus may be configured as an add-on (e.g., software and/or hardware-implemented) module of a neuromonitoring system that is employed for receiving and recording patient data. In some examples, the neuromonitoring data analysis apparatus may be comprised in the neuromonitoring system. In some further examples, the neuromonitoring data analysis apparatus may be external to the (intraoperative) neuromonitoring system. In some examples, all or some parts, components, and/or modules of the analysis apparatus may be implemented by the monitoring system. In some examples, none of the parts, components, and/or modules of the analysis apparatus may be implemented by the monitoring system.

Referring now to FIG. 1, a neuromonitoring data analysis apparatus 1000 may comprise an I/O device 1100, a processor 1200 and a memory 1300.

In some example implementations, the neuromonitoring data analysis apparatus may provide a user thereof with outputs via I/O device 1100 comprising one or more output devices. The one or more output devices may include, for example, devices that are configured to convert electrical signals into outputs that can be sensed as output by a human, such as sound, light, and/or touch. Output devices can include display screens, and/or audio output device(s) such as, for example, speaker(s) and/or earphones.

I/O device 1100 may further include one or more input devices which are configured to receive any type of data and/or information by converting, for example, or machine-generated signals and/or human-generated signals such as physical movement, physical touch or pressure, and/or the like, into electrical signals as input data into the computing system. Examples of such input devices include touch screens, microphones, hand gesture tracking devices, hand-held pointing devices (e.g., computer mouse, stylus) and/or the like.

I/O device 1100 may be employed to access data and/or information generated by the neuromonitoring data analysis apparatus 1000 and/or to provide inputs including, for instance, control commands, operating parameters, queries and/or the like. For example, I/O device 1100 may allow a user of a neuromonitoring system to subject the patient to one or more physical stimuli, for instance, via output electrode 1102. I/O device 1100 may further be configured to sense, via sensor 1104, signals which are generated in response to subjecting the patient to non-electric stimuli including, for example, sound for Auditory brainstem evoked potential, flashes for visual evoked potential, caloric and/or tactile stimulus. Sensed response signals can include, for example, such as SSEP and/or MEP. Output electrode 1102 may include one or more electrodes. Sensor 1104 may include one or more sensors comprising, e.g., electrodes.

Neuromonitoring data analysis apparatus 1000 may further include a processor 1200 and a memory 1300 which is configured to store data 1310 (e.g., patient data) and algorithm code and/or a machine learning (ML) model 1320. Processor 1200 may be configured to execute algorithm code and/or apply machine learning (ML) model 1320 for the processing of data 1310 resulting in the implementation of an intraoperative neuromonitoring data analysis (INDA) engine 1400. INDA engine 1400 may be configured to characterize a patient's neural functional state, e.g., as outlined herein and/or allow online labelling.

The term "processor", as used herein, may additionally or alternatively refer to a controller. Processor 1200 may be implemented by various types of processor devices and/or processor architectures including, for example, embedded processors, communication processors, graphics processing unit (GPU)-accelerated computing, soft-core processors, quantum-based processor and/or general purpose processors.

Memory 1300 may be implemented by various types of memories, including transactional memory and/or long-term storage memory facilities and may function as file storage, document storage, program storage, or as a working memory. The latter may for example be in the form of a static random access memory (SRAM), dynamic random access memory (DRAM), read-only memory (ROM), cache and/or flash memory. As working memory, memory 1300 may, for example, include, e.g., temporally-based and/or non-temporally based instructions. As long-term memory, memory 1300 may for example include a volatile or non-volatile computer storage medium, a hard disk drive, a solid state drive, a magnetic storage medium, a flash memory and/or other storage facility. A hardware memory facility may for example store a fixed information set (e.g., software code) including, but not limited to, a file, program, application, source code, object code, data, and/or the like.

Neuromonitoring data analysis apparatus 1000 may further comprise at least one communication module 1500 configured to enable wired and/or wireless communication between the various components and/or modules of the apparatus and which may communicate with each other over one or more communication buses (not shown), signal lines (not shown) and/or a network infrastructure. Communication module 1500 may be configured for enabling communication using one or more communication formats, protocols and/or technologies such as, for example, to internet communication, optical or RF communication, telephonybased communication technologies and/or the like. In some examples, communication module 1500 may include I/O device drivers (not shown) and network interface drivers (not shown) for enabling the transmission and/or reception of data over a network. A device driver may for example, interface with a keypad or to a USB port. A network interface driver may for example execute protocols for the Internet, or an Intranet, Wide Area Network (WAN), Local Area Network (LAN) employing, e.g., Wireless Local Area Network (WLAN)), Metropolitan Area Network (MAN), Personal Area Network (PAN), extranet, 2G, 3G, 3.5G, 4G, 5G, 6G mobile networks, 3GPP, LTE, LTE advanced, Bluetooth® (e.g., Bluetooth smart), ZigBee™, near-field communication (NFC) and/or any other current or future communication network, standard, and/or system.

Neuromonitoring data analysis apparatus 1000 may further include a power module 1600 for powering the various components and/or modules and/or subsystems of the apparatus. Power module 1600 may comprise an internal power supply (e.g., a rechargeable battery) and/or an interface for allowing connection to an external power supply.

It will be appreciated that separate hardware components such as processors and/or memories may be allocated to each component and/or module of neuromonitoring data analysis apparatus 1000. However, for simplicity and without be construed in a limiting manner, the description and claims may refer to a single module and/or component. For example, although processor 1200 may be implemented by several processors, the following description will refer to processor 1200 as the component that conducts all the necessary processing functions of neuromonitoring data analysis apparatus 1000.

Functionalities of neuromonitoring data analysis apparatus 1000 may be implemented fully or partially by a multifunction mobile communication device also known as "smartphone", a mobile or portable device, a non-mobile or non-portable device, a digital video camera, a personal computer, a laptop computer, a tablet computer, a server (which may relate to one or more servers or storage systems and/or services associated with a business or corporate entity, including for example, a file hosting service, cloud storage service, online file storage provider, peer-to-peer file storage or hosting service and/or a cyberlocker), personal digital assistant, a workstation, a wearable device, a hand-held computer, a notebook computer, a vehicular device, a non-vehicular device and/or a stationary device. For example, some of INDA engine 1400 functionalities may be implemented by on-premise (e.g., in a hospital or other clinical facility), and some by devices, apparatuses and/or system which are located off-premise (e.g., the "cloud"). Alternative configurations may also be conceived.

Various approaches may be adopted for implementing a machine learning model for employment by neuromonitoring data analysis apparatus 1000 of a neuromonitoring system. For example, the machine learning (ML) model may comprise a plurality of ML submodels. In examples, a ML submodel may relate to a certain level of the ML model. In some instances, the plurality of ML models may be organized in a hierarchical structure, e.g., as described herein in conjunction with FIGS. 2A and 2B. In some examples, a ML submodel may be feature-based, optionally requiring pre-processing of signals to perform feature-extraction. In some other examples, a ML submodel may be based on artificial neural networks (ANNs).

Figures 2A, 2B:
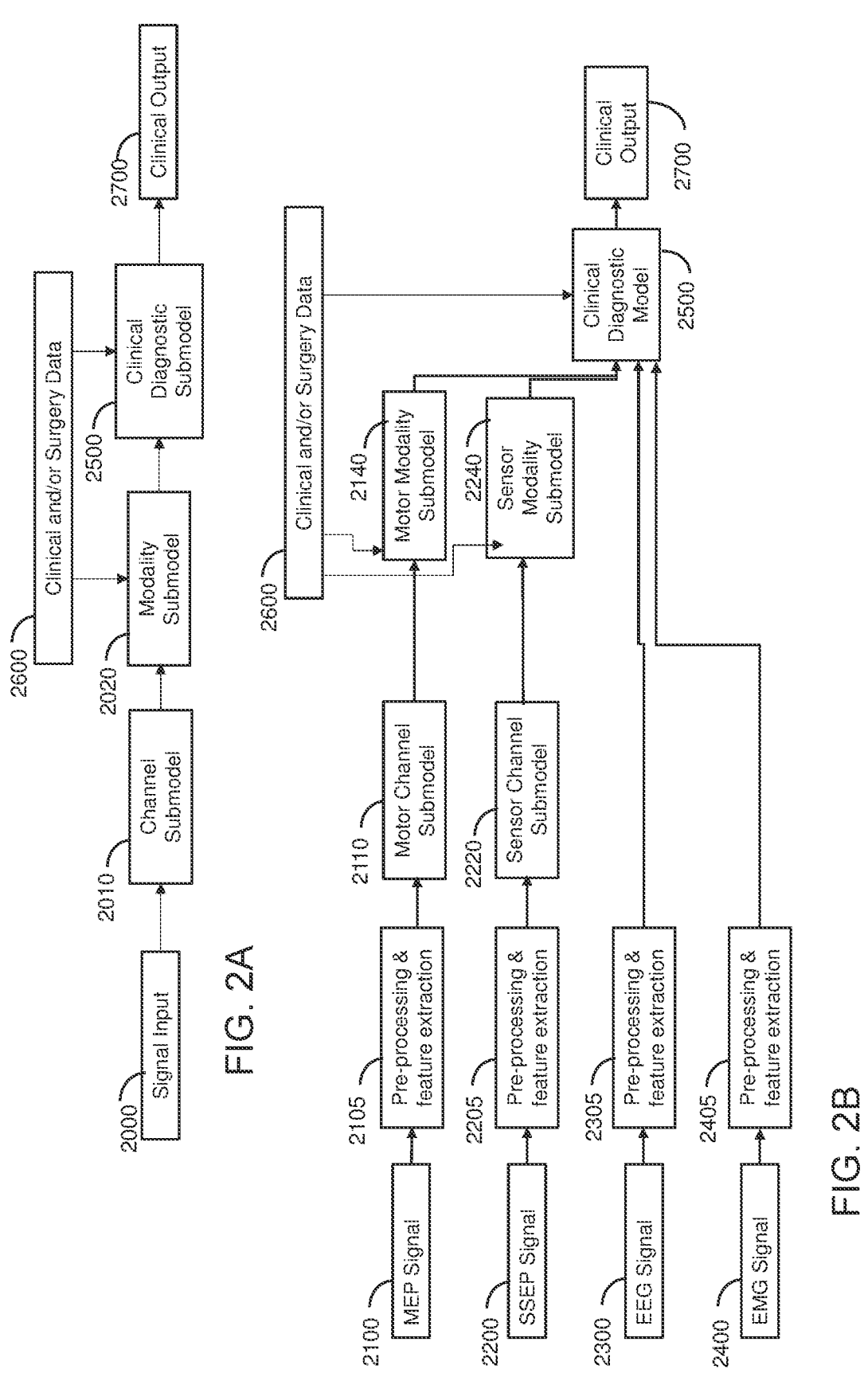
FIG. 2A shows a general block diagram illustration for creating a machine learning model for implementation by the neuromonitoring data analysis apparatus, according to an embodiment.
FIG. 2B shows a more specific block diagram illustration for creating the machine learning model for implementation by the neuromonitoring data analysis apparatus, according to an embodiment.

For example, as schematically illustrated in FIG. 2A, at least one first ML submodel (e.g., channel model 3010) may be created and applied for analyzing a selected of input signal 2000 of a signal modality.

A signal modality may for example pertain to a signal category encompassing one of MEP, SSEP, EMG, EEG, and/or the like, and different types of input signal may pertain to correspondingly different channels of a same signal modality. For example, different types or channels of MEP-modality signals can include, for example, Deltoid Left; Deltoid Right; Biceps Left/Right; Triceps Left/Right; Thenar Left; Thenar Right; Tibialis Anterior Left/Right; Quadriceps—Tibialis Anterior Left/Right.

In order to distinguish between different channel submodels 2010 employed for analyzing signals of respective channels of a signal modality, capital alphabetic characters are added after the numerals, for example, first channel submodel 2010A, second channel submodel 2010B, third channel submodel 2010C. However, when there is no need to particularly distinguish each of the channel models, they are simply and collectively referred to as channel submodel 2010.

In some examples, at least one first ML submodel (or "at least one first channel submodel 2010A") may be applied for analyzing a first MEP input signal, at least one second channel submodel 2010B may be applied for analyzing a second MEP input signal, and so forth.

As a second level, at least one modality submodel 2020 may be employed for analyzing the signals of a certain modality (e.g., MEP modality, SSEP modality) as a whole. For example, a MEP modality submodel may be employed for analyzing a plurality of signals of the selected modality to provide, for the MEP modality, a modality prediction. The at least one modality submodel 2020 may receive predictions (e.g., labels) produced by the at least one first ML submodel or channel submodel 2010.

As a third level, at least one clinical diagnostic submodel 2500 may be employed. The at least one clinical diagnostic submodel 2500 may receive predictions produced by the at least one modality submodel 3030 of the second level to provide, based thereon, a clinical output 2700.

In some examples, the at least one modality submodel 2020 and/or clinical diagnostic submodel 2500 may be complemented with clinical and/or surgery data 2600 for analyzing the modality predictions to produce clinical output 2700.

As exemplified a in FIG. 2B, in a first level, a certain signal of a selected modality (e.g., a MEP signal 2100, SSEP signal 2200, EEG signal 2300, and/or EMG signal 2400) may be received by the corresponding channel submodel. For example, motor channel submodel 2110 may receive an MEP signal 2100, and a sensor channel submodel 2220 may receive an SSEP signal 2200.

In some examples, the input signal may be preprocessed for feature extraction purposes. For example, MEP signal 2100 may be preprocessed to perform feature extraction (block 2105) for at least one MEP signal, and SSEP signal 2200 may be preprocessed to perform feature extraction (2205) for at least one SSEP signal. As mentioned, an ML model such as motor channel submodel may not necessarily be feature-extraction based, but can be based on deep learning ML models such as artificial neural networks.

Furthermore, in a second level, analysis output produced by the motor channel submodel 2110 is provided to a motor modality submodel 2140 for further analysis thereby, and analysis output produced by sensor channel submodel 2210 is provided to sensor modality submodel 2240 for further analysis thereby. Optionally, the input to a second level ML submodel is the output of the 1$^{st}$ level ML model. Based on the input of the 1$^{st}$ ML models, the 2$^{nd}$ level ML submodels determine, for example, whether there is a significant change in the signals requiring the expert's attention, or not.

The analysis outputs produced by motor modality submodel 2140 and sensor modality submodel 2240 are provided to clinical diagnostic submodel 2500 for further analysis thereby to obtain a clinical output representing a clinical interpretation of the data provided to the various ML submodels.

In some examples, clinical and/or surgery data may be provided to the (e.g., MEP and/or SSEP) modality submodels and/or to the clinical diagnostic submodel 2500 for producing clinical output 2700. In some examples, data relating to EEG signals 2300 and/or EMG signals 2400 may be provided to clinical diagnostic model 2500. In some examples, EEG signals 2300 and EMG signals 2400 may be preprocessed for feature extraction purposes (blocks 2305 and 2405, respectively).

The following three examples pertains to scenarios where the apparatus correctly identifies anomalies in signals as clinically significant, i.e., as injury of neural structures:

In an example scenario, the apparatus identifies impairment of corticospinal tract function during cervical laminectomy, also referred to as central cord syndrome. The apparatus may identify a marked decrease of motor response up to the point of response disappearant from the right hand and leg muscles and, optionally, classifies the anomaly as the central cord syndrome.

In an example scenario, impairment of corticospinal tract function during cervical laminectomy, also known as Brown-Séquard syndrome, is identified by the apparatus. A marked decrease of motor response up to the point of response disappearant from the hand muscles bilaterally is identified by the apparatus and, optionally, classified as Brown-Séquard syndrome.

In an example scenario, the apparatus identifies impairment of C5\C6 nerve function during cervical laminectomy. The data are descriptive of signals displayed by the monitoring system and showing a marked decrease of motor response from the right bicep muscle. Prominent baseline responses and "current" response may be displayed by the monitoring system using different colors.

The following two examples pertain to scenarios where anomalies in the signals do not pertain to neural structural injury but to decreased motor responses caused by systemic effects. Hence, the detected anomalies are not clinically significant with respect to neural structure injury:

An example scenario pertains to impairment of corticospinal tract function demonstrated from baseline testing in right leg. A marked decrease of motor response in hands muscles and moderate in arm and leg muscles are displayed, which is demonstrated due to anesthetic and blood pressure changes.

Another example scenario pertains to impairment of corticospinal tract function demonstrated from baseline testing in right leg. A marked decrease of motor response in left hand and foot muscles is demonstrated due to anesthetic and blood pressure changes. There are no baseline responses and no "current" responses displayed in right leg channels, and there is displayed a marked decrease in "current" responses on left channels. Hence, the decrease in motor response represented by the signals displayed by the monitoring system due to systemic effects and preoperative disfunction.

The following four examples pertain to data descriptive of signals with associated false-positive alerts indicating neural structural injury as provided by prior art neuromonitoring data analysis apparatuses, e.g., with respect to cervical fusion.

These four examples below demonstrate that prior art apparatuses oftentimes falsely identify or falsely classify clinically insignificant anomalies (anomalies not related to neural structure injury) in signals, as clinically significant (e.g., relating to neural structural injury). This is, for example, because prior art apparatuses may use rule-based criteria such as "peak-to-peak" of an individual signal, rely only on the comparison of a selected "current" signal against a corresponding baseline signal, an area-under-the-curve model, or similar. By contrast, embodiments of the analysis apparatus presented herein take into consideration (e.g., collectively analyzes) data descriptive of a plurality of different or distinct signals sensed by the monitoring system for correctly identifying injury, for example by a trained machine learning model, optionally in combination with a rule-based approach.

In an example scenario, a prior art apparatus displays Motor responses at baseline in one color and "current" motor responses using a second color different from the first color. The prior art apparatus outputs "alerts" or "flags" (e.g., "red flags" at corresponding timestamp or portion of a signal plot displayed by the neuromonitoring system) of non-important changes which are mistakenly identified by the prior art apparatus as clinically significant changes in the signal with respect to neural structure injury. In addition, the prior art analysis apparatus falsely identifies technical stimulus-induced artifacts as responses.

In a further example scenario Motor responses at baseline (first color) and "current" (second color) may be displayed. The prior art analysis apparatus outputs Alerts ("Red flags") in association with non-important changes (e.g., clinically insignificant changes with respect to neural structure injury), putatively due to systemic-anesthetic changes. The prior art analysis apparatus may also mistakenly identify technical stimulus-induced artifact as a response.

In a further example scenario, the prior art analysis apparatus, technical stimulus-induced artifacts at baseline are mistakenly identified or measured as a response, and its disappearance in the "current" response causes false-positive alerts.

In another example scenario, a prior art analysis apparatus marks or produces an alert with respect to non-important changes (e.g., clinically insignificant changes with respect to neural structure injury) in somatosensory responses.

Figure 3:
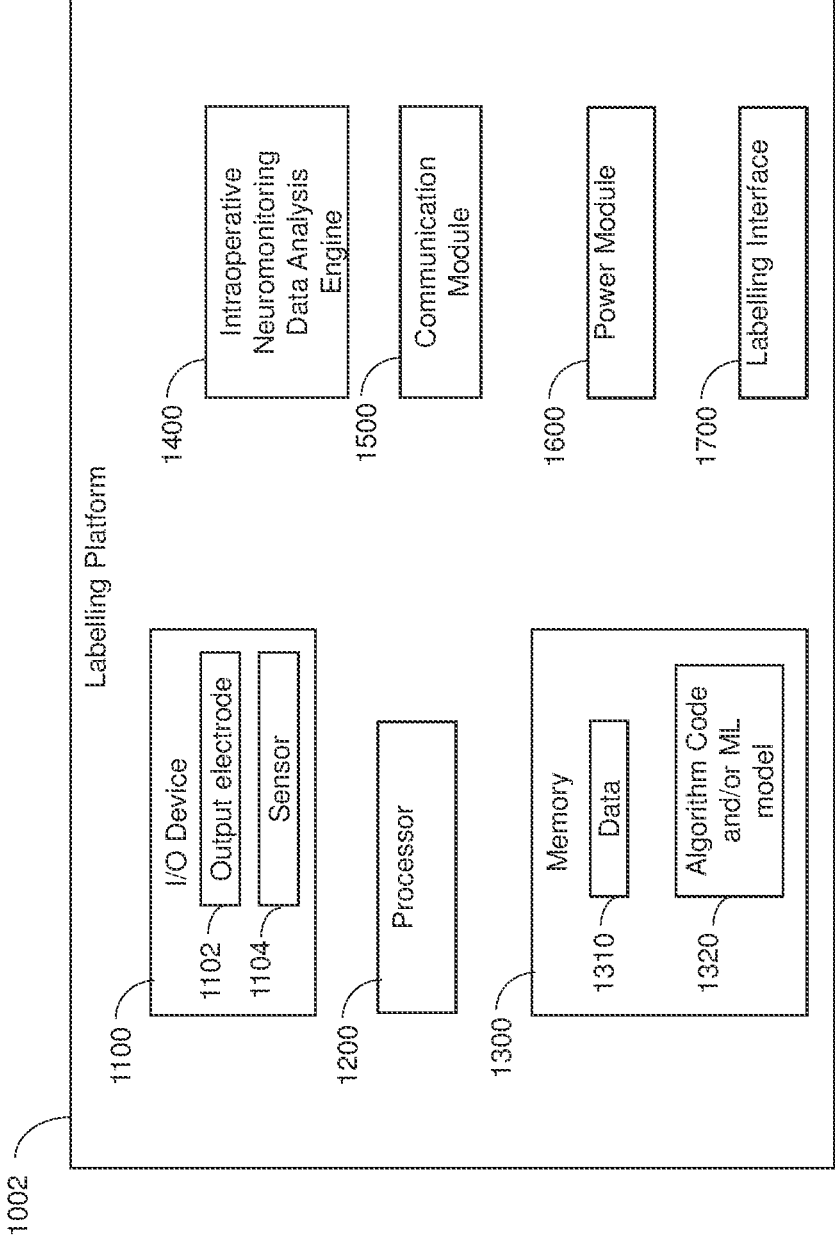
FIG. 3 is a schematic block diagram illustration of a neuromonitoring labelling platform, according to some embodiments.

Further referring now to FIG. 3, a neuromonitoring labelling platform 1002 may be configured to have a labelling interface 1700 enabling online or on-the-fly, (e.g., real or simulated interoperative) labelling capabilities.

For example, I/O device 1100 may also include one or more device interfaces (e.g., one or more touch screens) enabling an expert to perform "on-the-fly" or real-time labelling of neuromonitoring data, in a real-life surgery setting. For instance, I/O device 1100 may display user-selectable fields allowing an expert to perform online labelling of displayed signals and/or data, for example, as schematically shown with respect to FIGS. 4-6, which schematically illustrate various fields that may be displayed by I/O device 1100.

Figure 4:
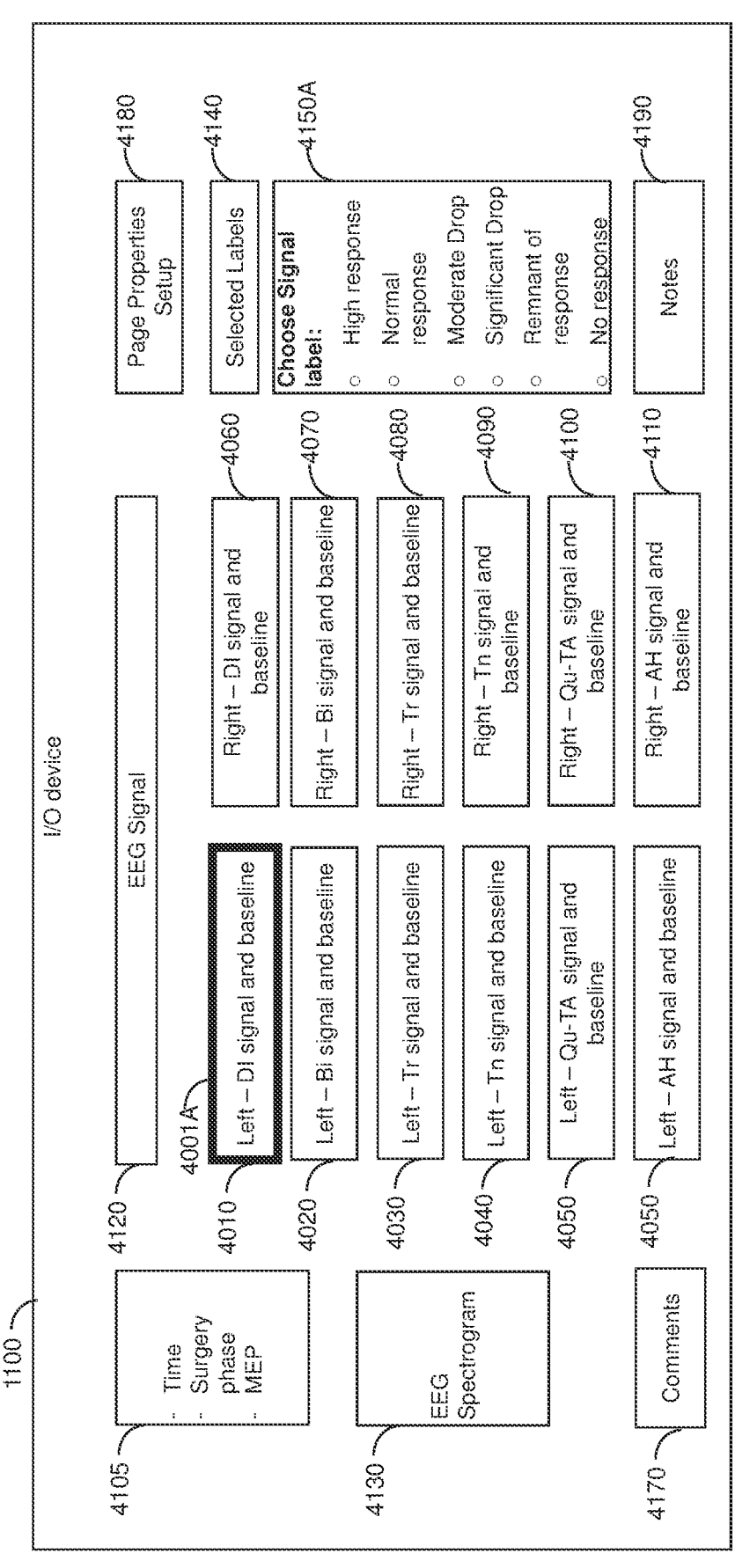
FIG. 4 is a schematic block diagram illustration of a screenshot displaying plots of signals that are analyzed by the neuromonitoring data analysis apparatus, according to some embodiments.

FIG. 4 schematically illustrates the various fields that may be displayed by I/O device 1100, where the expert selected a specific signal or channel representing, e.g., "Left-DI signal and baseline". It is noted that in some examples, the apparatus may not comprise a display yet may be configured to an output of a system configured to produce the various signals. The apparatus may operably communicate with the system for performing analysis of data descriptive of signals displayed as graphs by the system.

The various channel fields show corresponding signal plots such as measured signal and related baseline. However, merely to simplify the discussion, the plots have been removed and were replaced with a corresponding description of the plots. For instance, field 4010 has been annotated as "Left-DI signal and baseline".

Depending on the data or signal fields selected by the expert, different selectable labelling options are automatically displayed by I/O device 1100.

For example, as schematically shown in FIG. 4, when a certain channel such as Left-Di signal and baseline 4010 is selected by the expert, I/O device 1100 displays corresponding channel-labelling options 4150A, which are expert-selectable fields, annotated by various labels relating to various channel-related scenarios such as, for example, "High Response", "Normal Response", "Moderate Drop", "Significant Drop", "Remnant of Response" and "No response". The selection made is schematically illustrated by bold rectangle 4001A. Accordingly, based on analysis of a plurality of signals, the analysis apparatus may be configured to classify at least one of a plurality of signals to fall into corresponding categories and, optionally, provide corresponding outputs.

Figure 5:
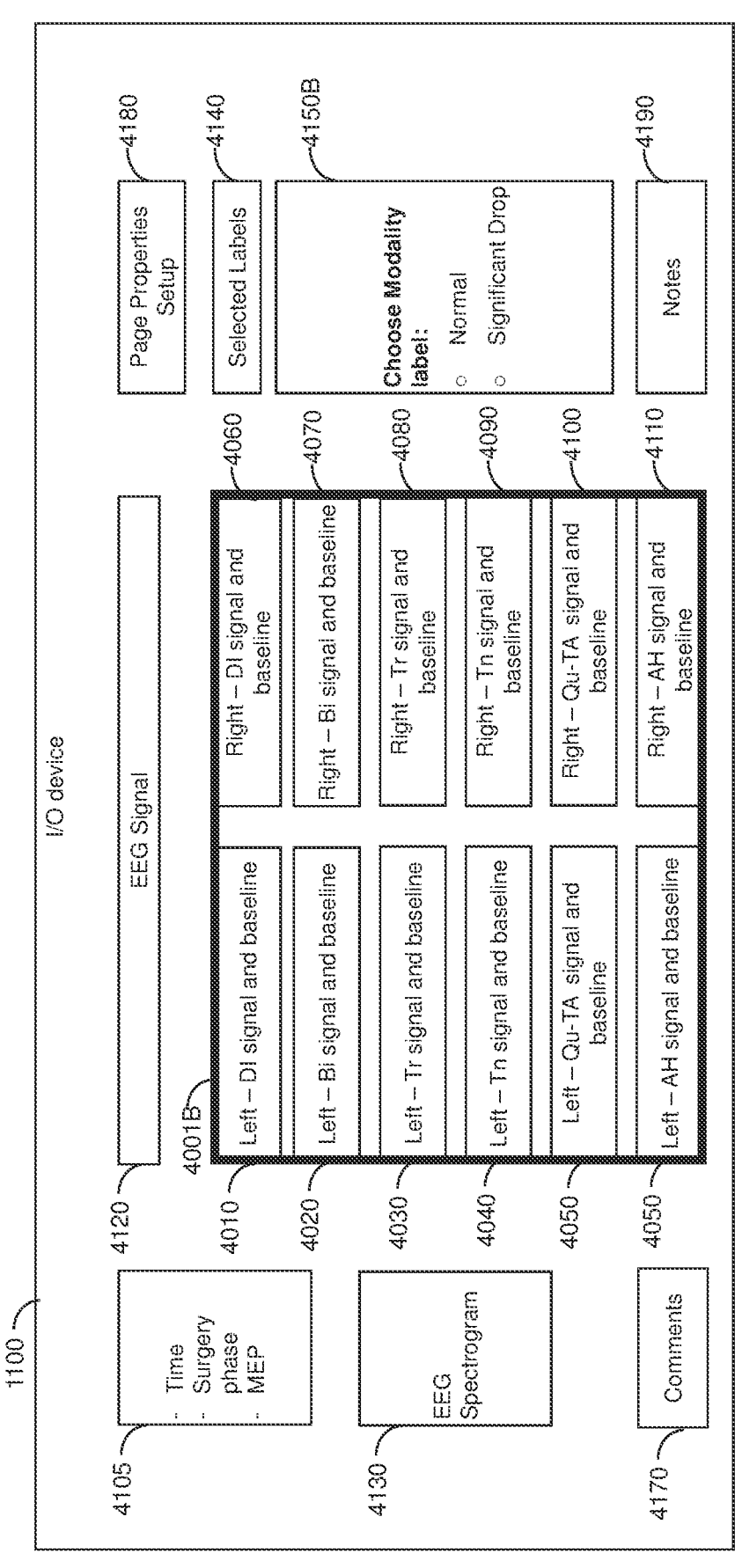
FIG. 5 is a schematic block diagram illustration of another screenshot displaying plots of signals analyzed displayed by the neuromonitoring data analysis apparatus, according to some embodiments.

In another example, as schematically shown in FIG. 5, when the expert selects all signals of a certain modality (e.g., MEP signals 4010-4110), I/O device 1100 displays corresponding modality-labelling options 4150B annotated by various labels relating to various modality-related scenarios which may be one of, for example, "Normal" and "Significant Drop". The selection made is schematically illustrated by bold rectangle 4001B. Accordingly, based on analysis of a plurality of signals, the analysis apparatus may be configured to classify at least one of a plurality of signals to fall into corresponding categories and, optionally, provide corresponding outputs.

Figure 6:
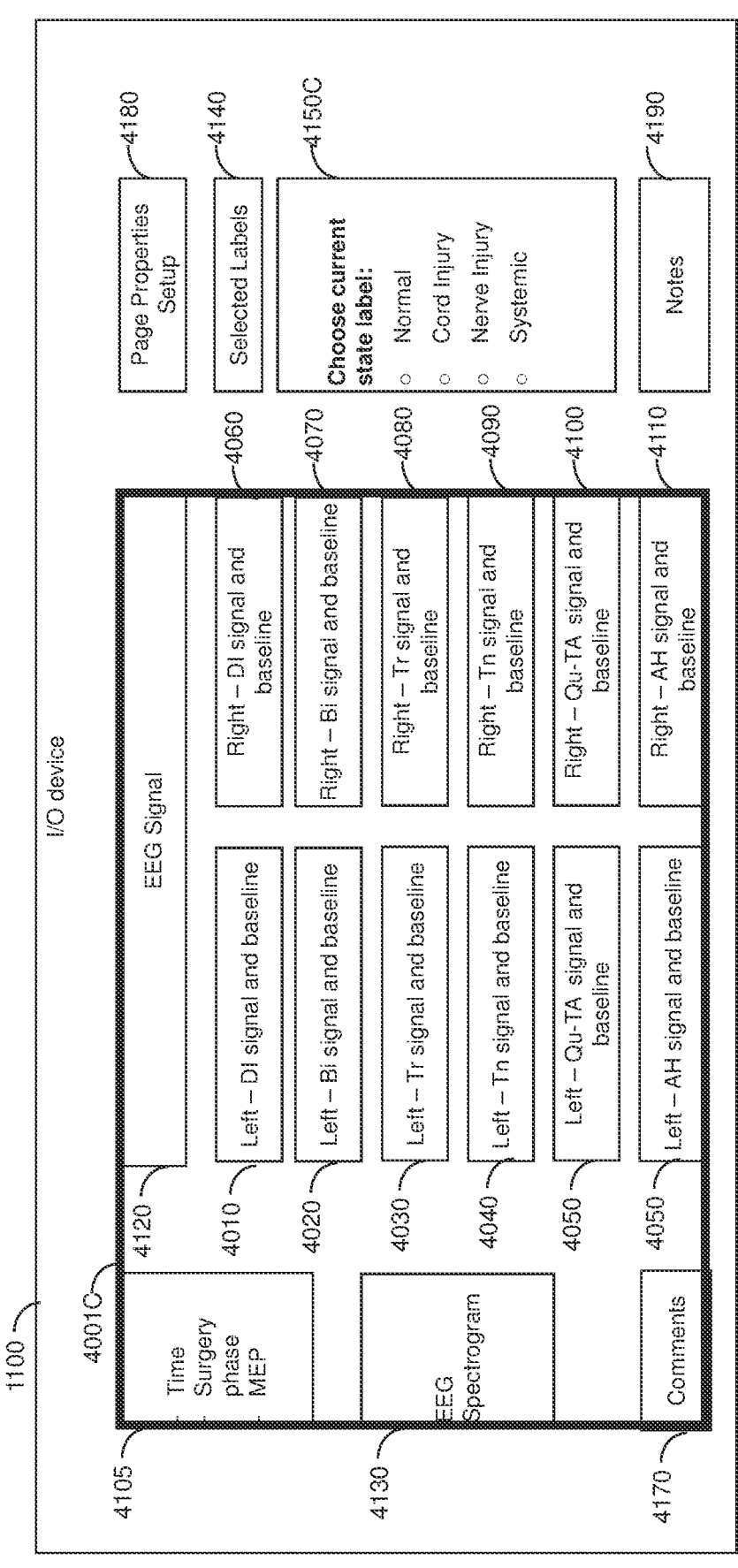
FIG. 6 is a schematic block diagram illustration of another screenshot displaying plots of signals analyzed by the neuromonitoring data analysis apparatus, according to some embodiments.

In a yet further example, as schematically shown in FIG. 6, when the expert selects all signals of all modalities, I/O device 1100 displays corresponding clinical-interpretation labelling options 4150C annotated by various labels relating to various clinical scenarios which may be one of, for example, "Normal", "Cord Injury", "Nerve Injury" and "Systemic". A selection of all signals is schematically illustrated by bold rectangle 4001C. Correspondingly, in some examples, the analysis apparatus may classify, based on the collective analysis of a plurality of signals relating to at least two neural structures, a state of at least one signal of the plurality of signals, to fall into one of the following categories: "Normal", "Cord Injury", "Nerve Injury", and "Systemic" and, optionally, provide corresponding outputs.

In some examples, I/O device 1100 may display a checkbox annotated "Technical Problem" to indicate whether one of the selected scenarios is linked to a technical problem or not.

Additional fields that may be displayed by I/O device 1100 include, for example, a title and time field 4105 displaying the present time and information about the displayed modality, an EEG signal field 4120, an EEG spectrogram field 4130, a selected label display field 4140, a general comments field 4170, a page properties configuration field 4180, and a notes field 4190 for entering notes on the selected labels.

Further referenced is now made to FIG. 7. A method for analyzing data descriptive of signals in a nervous system of a patient undergoing a medical procedure may, in some embodiments, include receiving data descriptive of a plurality of neurophysiological response signals generated in at least two (e.g., distinct or different) neural structures (e.g., relating to different pathways) of a patient as a result of subjecting the patient to a plurality of physical stimuli (block 7100).

In some embodiments, the method may further include identifying, based on the received data, an anomalous event that is indicative of injury of at least one of the at least two neural structures (block 7200).

In some embodiments, the method may include providing a first output relating to the identified event (block 7300).

ADDITIONAL EXAMPLES

Example 1 pertains to a neuromonitoring data analysis apparatus configured to analyze neuromonitoring signals of a subject's nervous system, the apparatus comprising: at least one processor; and at least one memory configured to store data and software code portions executable by the at least one processor to cause to perform: receiving patient data comprising: data that are descriptive of at least one physical stimulus applied to a mammalian subject for responsively generating at least one signal in a plurality of neural structures of the subject's nervous system; and sensor data descriptive of at least one neurophysiological response signal generated in response the applied physical stimulus; determining, based on the received patient data descriptive of the at least one physical stimulus and the generated response signal, at least one characteristic with respect to at least one of the plurality of neural structures of the patient. Optionally, a machine learning model including multiple levels of hierarchically arranged machine learning submodels is employed for analyzing the received patient data.

Example 2 includes the subject matter of Example 1 and, optionally, wherein the at least one characteristic pertains to the functional state of a neural structure.

Example 3 includes the subject matter of examples 1 and/or 2 and, optionally, wherein the neural structure of the plurality of neural structures comprises a neural pathway and/or receptors.

Example 4 includes the subject matter of any one or more of the examples 1 to 3 and, optionally, comprising at least one classifier for determining the neural functional state.

Example 5 includes the subject matter of example 4 and, optionally, employing a machine learning model comprising, e.g., Gradient Boosting and/or artificial neural networks.

Example 6 includes the subject matter of Example 5 and, optionally, comprising an interface allowing an expert, during a surgical procedure, associating the received patient data descriptive of the at least one physical stimulus and the generated response signal with one or more labels for training of the machine learning model, the one or more labels relating to characteristic of the patient's nervous system.

Example 7 includes the subject matter of examples 4 and/or 5 and, optionally, configured to classify the neural functional state into one of the following: "NORMAL", "DROP" or "DISAPPEAR".

Example 8 includes the subject matter of any one or more of the Examples 1 to 7 and, optionally, wherein the at least one physical stimulus pertains to one of the following: an evoked potential; a reflex; a spontaneous potential, or any combination of the above.

Example 9 includes the subject matter of any one or more of the Examples 1 to 8 and, optionally, wherein the memory is configured to receive patient data further comprising one of the following: clinical patient data; demographic patient data; anesthesia data; physiological patient data; surgical data; baseline motor evoked potential signal data; baseline EMG signals; baseline EEG signals; baseline somatosensory evoked potential signal data; reflexes; or any combination thereof.

Example 10 includes the subject matter of any one or more of the examples 1 to 9 and, optionally, wherein the information further includes clinical information descriptive of one of the following: systemic physiological states; a system malfunction; or both.

Example 11 includes the subject matter of any one or more of the examples 1 to 10 and, optionally, further configured to characterize a pathway injury as relating to one of the following: motor insult including motoric injury impact location; somatosensory insult, including sensory impact location; cord pathway injury severity, including complete or incomplete injury; or any combination thereof.

Example 12 includes the subject matter of any one or more of the examples 1 to 11 and, optionally, further configured to characterize injury of the at least one neural structure as relating to one of the following: Myotome injury; nerve injury severity, including complete or incomplete injury.

Example 13 includes the subject matter of any one or more of the examples 1 to 12 and, optionally, wherein the at least one characteristic is provided to a user in real-time or in near real-time.

Example 14 includes the subject matter of any one of the examples 1 to 13 and, optionally, further configured to provide an operational recommendation output comprising one of the following: evoke additional motor evoked potential; evoke additional somatosensory evoked potential; change stimulus intensity of the additional motor evoked potential; change stimulus intensity of the additional somatosensory evoked potential; update recording parameters; check for neuromonitoring system malfunction; check impedance; check anesthesia parameters; to perform peripheral nerve stimulation; check physiological parameters; check patient position; hold surgical procedure; change and/or check electrode positioning; patient positioning; or any combination of the aforesaid.

Example 15 includes the subject matter of any one or more of the examples 1 to 14 and, optionally, wherein the apparatus is configured to be employable intraoperatively.

Example 16 includes the subject matter of any one or more of the examples 4 to 15 and, optionally, wherein the machine learning model comprises a plurality of machine learning submodels.

Example 17 includes the subject matter of Example 7 and, optionally, wherein a first level of machine learning submodels of the hierarchically arranged machine learning submodels is configured to analyze signals of a plurality of channels pertaining to a signal modality to produce a plurality of respective channel-wise analysis outputs.

Example 18 includes the subject matter of example 17, wherein a second level of machine learning submodels of the hierarchically arranged machine learning submodels is configured to receive the plurality of channel-wise analysis outputs; and wherein the second level of machine learning submodules is configured to analyze the plurality of received channel-wise analysis outputs of the signal modality to provide an analysis output descriptive of the modality.

Example 19 includes the subject matter of Example 18 and, optionally, wherein a third level of machine learning submodules of the hierarchically arranged submodules receives the analysis output descriptive of the modality; and wherein the third level of machine learning submodules is configured to analyze the output received from the second submodule to produce an output descriptive of a clinical interpretation of the received patient data.

Example 20 includes a method for performing neuro-monitoring data analysis, the method comprising:

receiving patient data comprising:

data that are descriptive of at least one physical stimulus applied to a mammalian subject for responsively generating at least one signal in a plurality of neural structures of the subject's nervous system; and sensor data descriptive of at least one neurophysiological response signal generated in response the applied physical stimulus;

determining, based on the received patient data descriptive of the at least one physical stimulus and the generated response signal, at least one characteristic with respect to at least one of the plurality of neural structures of the patient. Optionally, the determining includes employing a machine learning model having multiple levels of hierarchically arranged machine learning submodels for analyzing the received patient data.

Example 21 includes the subject matter of example 20 and, optionally, wherein the at least one characteristic pertains to a functional state of a neural structure.

Example 22 includes the subject matter of example 20 and/or example 21 and, optionally, wherein the determining includes classifying the neural functional state.

Example 23 includes the subject matter of any one or more of the examples 21 to 23 and, optionally, wherein the determining comprises employing a machine learning model for analyzing the patient data.

Example 24 includes the subject matter of any one or more of the examples 22 to 23 and, optionally, classifying the neural functional state into one of the following: "NORMAL", "DROP" or "DISAPPEAR".

Example 25 includes the subject matter of any one or more of the examples 20 to 24 and, optionally, providing an operational recommendation output comprising one of the following:

evoke additional motor evoked potential;

evoke additional somatosensory evoked potential;

change stimulus intensity of the additional motor evoked potential;

change stimulus intensity of the additional somatosensory evoked potential;

update recording parameters;

check for neuromonitoring system malfunction;

check impedance;

check anesthesia parameters;

to perform peripheral nerve stimulation;

check physiological parameters;

check patient position;

hold surgical procedure;

electrode positioning;

patient positioning; or any combination of the aforesaid.

Example 26 includes the subject matter of any one or more of the examples 20 to 25 and, optionally, comprising intraoperatively performing data analysis of the patient data.

Example 27 includes the subject matter of any one or more of the examples 23 to 26 and, optionally, wherein the machine learning model comprises a plurality of machine learning submodels.

Example 28 includes the subject matter of example 27 and, optionally, analyzing analyze signals of a plurality of channels pertaining to a signal modality to produce a plurality of respective channel-wise analysis outputs by a first level of machine learning submodels of the hierarchically arranged submodels.

Example 29 includes the subject matter of example 28 and, optionally, receiving the plurality of channel-wise analysis outputs by a second level of machine learning submodules of the hierarchically arranged submodels, and analyzing by the second level of machine-learning modules the plurality of received channel-wise analysis outputs of the signal modality to provide an analysis output descriptive of the modality.

Example 30 includes the subject matter of example 29 and, optionally, receiving, at a third level of machine learning submodules of the hierarchically arranged submodules, the analysis output descriptive of the modality; and analyzing, by the third level of machine learning submodules, the output received from the second submodule to produce an output descriptive of a clinical interpretation of the received patient data.

Example 31 includes a method comprising: receiving patient data on a neuromonitoring labelling platform associated with a neuromonitoring system, during runtime of the neuromonitoring system; displaying information related to the received patient data on a display of an input-output (/O) device of the labelling platform; labeling the patient data using the I/O device during the runtime; wherein the one or more labels relate to characteristic of a patient's nervous system.

Example 32 includes the subject matter of example 31 and, optionally, wherein the labelling is performed intraoperatively for labelling of patient data received from a neuromonitoring system for training a machine learning model of the neuromonitoring data analysis apparatus.

Example 33 includes the subject matter of example 31 and/or 32 and, optionally, wherein the labeling comprises selecting a portion of the displayed information by dragging one or more windows on the display on the I/O device.

Example 34 includes the subject matter of any one or more of the examples 31 to 33 and, optionally, wherein the labeling comprises selecting a portion of the displayed information by touch-pressing the display on the I/O device.

Example 35 includes the subject matter of any one or more of the examples 31 to 34 and, optionally, wherein the labeling comprises selecting a portion of the displayed information by providing a voice input to the I/O device.

Example 36 includes the subject matter of any one or more of the examples 31 to 35 and, optionally, wherein the labeling comprises selecting a portion of the displayed information by providing a gaze-based input to the I/O device.

Example 37 includes the subject matter of any one or more of the examples 31 to 36 and, optionally, wherein the labeling comprises selecting a portion of the displayed information based on an association between the selected information and a corresponding hierarchical level of the selected information in a machine learning model comprising multiple levels of hierarchically arranged machine learning submodules.

In some examples, a neuromonitoring data analysis apparatus is configured to perform the following steps: subjecting a mammal to a plurality of neural physical stimuli in a plurality of neural structures of or relating to, e.g., different or distinct pathways; analyzing data that are descriptive of a plurality of neurophysiological response signal generated in association with the plurality of neural structures in the mammal in response to subjecting the mammal to the one or more neural stimuli; determining whether the detected anomaly is indicative of injury of at least one of the at least two neural structures, or not; and, optionally, providing an output in the event that the detected anomaly is indicative of injury of the at least one neural structure. Different pathways may for example pertain to different motor and/or sensory and/or parasympathetic and/or sympathetic pathways. In some examples, "different pathways" may pertain to different pathways of a same category (different motor pathways) or of different categories (motor and sensory pathway).

In some examples a neuromonitoring data analysis apparatus configured to monitor a subject's nervous system, comprises: at least one processor; and at least one memory configured to store data and software code portions executable by the at least one processor to cause to perform: receiving patient and sensor data; identifying, based on the received patient data, an anomalous event that is indicative of injury of at least one of the at least two neural structures; and providing a first output relating to the identified event.

In some examples, patient data are descriptive of a plurality of physical stimuli applied to at least two neural structures of the mammalian subject's nervous system. In some examples, sensor data are descriptive of a plurality of neurophysiological response signals generated in the at least two neural structures in response to the applying of the plurality of physical stimuli.

In some examples, the step of identifying is further based on the sensor data that are descriptive of the plurality of physical stimuli, optionally simultaneously applied to a plurality of neural structures.

In some examples, the step of identifying comprises distinguishing between: 1) a first anomalous event relating to injury of at least one of the at least two neural structures; and 2) a second anomalous event not relating to injury of at least one of the at least two neural structures.

In examples, by taking into consideration the plurality of neurophysiological response signals generated in the at least two neural structures and, optionally, the data descriptive of the applied physical stimuli, a false-positive rate of anomalous events identified as relating to injury of a neural structure is reduced, compared to a false-positive rate obtained if each response signal was analyzed individually.

In some examples, by taking into consideration a plurality of neurophysiological response signals generated by and/or in the at least two neural structures, and, optionally, data descriptive of the applied physical stimuli a false-negative rate of anomalous events identified as relating to injury of a neural structure is reduced, compared to a false-negative rate obtained if each response signal was analyzed individually.

In some examples, the identifying comprises: classifying an anomalous event to fall into one of the following categories: a first anomalous event relating to injury and/or of insult of at least one of the at least two neural structures; and a second anomalous event not relating to injury of at least one of the at least two neural structures.

In some examples, the first output includes information about a probability that the detected anomalous event relates injury of the at least one neural structure.

In some examples, the apparatus is configured to provide a second output descriptive of the second anomalous event.

In some examples, an output descriptive of the second anomalous event includes information as to whether the second anomalous event pertains to one of the following: a sensor misconfiguration; a signal artifact, a systemic physiological factor, system malfunction, environmental factor, or any combination of the aforesaid.

In some examples, a systemic factor includes one or more of the following: patient anesthesia; blood pressure; patient position; patient posture; or any combination of the aforesaid.

In some examples, the first anomalous event relates to a functional state of a neural structure.

In some examples, a neural structure comprises a neural pathway and/or receptors.

In some examples, the first anomalous event pertains to a neural functional state as falling into one of the following categories: "DROP" or "DISAPPEAR".

In some examples, the second anomalous event includes a classification of a functional state of the least one neural structure as "NORMAL".

In some examples, the plurality of physical stimuli relate to one of the following: an evoked potential; a reflex; a spontaneous potential, or any combination of the above.

In some examples, a neuromonitoring data analysis apparatus is configured to: receive patient data comprising data that are descriptive of a plurality of physical stimuli applied to at least two neural structures of the mammalian subject's nervous system; and sensor data descriptive of a plurality of neurophysiological response signals generated in the at least two neural structures in response to the applying of the plurality of physical stimuli. The apparatus is further configured to (e.g., collectively) analyze the plurality of neurophysiological response signals; identifying, based on the (e.g., collectively) analyzing, an anomalous event that is indicative of injury and of at least one of the at least two neural structures; and, optionally, providing a first output relating to the identified event. In some examples, the expression "collectively analyzing" pertains to analyzing a larger amount of data descriptive of various signals for detecting and classifying an anomaly in one or more of the analyzed signals. By taking into consideration the contribution of a comparatively large number signals, the false-positive ratio (e.g., classification of anomalies as neural structure injury) is reduced compared to in approaches where a comparatively small number of signals is analyzed for anomaly detection and classification.

In some examples, the analyzing includes (e.g., collectively) analyzing: data that are descriptive of the plurality of response signals and descriptive of the physical stimuli applied to the at least two neural structures for generating the plurality of response signals.

In some examples, by taking into consideration (e.g., collectively analyzing) the plurality of neurophysiological response signals generated in the at least two neural structures and, optionally, data descriptive of the applied physical stimuli, a false-positive rate of anomalous events identified as relating to injury of a neural structure is reduced, compared to a false-positive rate that would be obtained if each response signal was analyzed individually. In some examples, by taking into consideration the plurality of neurophysiological response signals generated in the at least two neural structures and, optionally, the data descriptive of the applied physical stimuli, a false-negative rate of anomalous events identified as relating to injury of a neural structure is reduced, compared to a false-negative rate that would be obtained if each response signal was analyzed individually.

In some examples, the neuromonitoring data analysis apparatus is configured such that in the event it is determined that the detected anomaly does not relate to injury of the at least one neural structure, a second output is provided including information about the detected anomaly.

In some examples, the first output is indicative of a probability that the detected anomaly is indicative of injury and/or insult of the at least one neural structure.

In some examples, the injury of the at least one neural structure possibly causing a functional deficit, is the result of physical engagement (surgical engagement) with tissue region including the at least one neural structure.

In some examples, the apparatus is configured to detect an anomaly by comparing the generated response signals against corresponding baseline signals.

In some examples, the apparatus includes a classifier for classifying a neural functional state of the at least one neural structure into one of the following categories: "NORMAL", "DROP", "DISAPPEAR".

In some examples, a neuromonitoring data analysis apparatus is configured to perform: receiving patient data comprising: data that are descriptive of a plurality of physical stimuli applied to at least two neural structures of the mammalian subject's nervous system; and sensor data descriptive of a plurality of neurophysiological response signals generated in the at least two neural structures in response to the plurality of applied physical stimuli; determining whether a detected anomaly in data descriptive of the response signals is indicative of injury of at least one of the at least two neural structures, or not; and in the event it is determined by the apparatus that the detected anomaly relates to injury of the at least one neural structure, the apparatus optionally provides a first output including information about the injury of the at least one neural structure.

In some examples, patient data is descriptive of one of the following: clinical patient data; demographic patient data; anesthesia data; physiological patient data; surgical data; baseline motor evoked potential signal data; baseline EMG signals; baseline EEG signals; baseline somatosensory evoked potential signal data; reflexes; or any combination of the aforesaid.

In some examples, the first output includes information characterizing a pathway injury as relating, for example, to one of the following: motor insult including motoric injury impact location; somatosensory insult, including sensory impact location; cord pathway injury severity, including complete or incomplete injury; or any combination of the aforesaid. In some examples, the apparatus is configured to characterize injury of the at least one neural structure as relating to one of the following: Myotome injury; and/or nerve injury severity, including complete or incomplete injury.

In some examples, the second output of the anomalous event includes clinical information descriptive of one: a systemic physiological states; a neuromonitoring system malfunction; or both.

In some examples, the apparatus is configured to provide an operational recommendation output comprising one of the following: evoke additional motor evoked potential; evoke additional somatosensory evoked potential; change stimulus intensity of the additional motor evoked potential; change stimulus intensity of the additional somatosensory evoked potential; update recording parameters; check for neuromonitoring system malfunction; check impedance; check anesthesia parameters; to perform peripheral nerve stimulation; check physiological parameters; check and/or (how to) change patient position and/or posture; hold surgical procedure; electrode positioning; or any combination of the aforesaid. In some examples, the operational recommendation output depends on the identified anomaly.

In some examples, the apparatus includes a plurality of hierarchically configured machine learning submodels. A first level of machine learning submodels of the hierarchically arranged machine learning submodels may be configured to analyze signals of a plurality of channels pertaining to a signal modality to produce a plurality of respective channel-wise analysis outputs. A second level of machine learning submodules of the hierarchically arranged machine learning submodels may be configured to receive the plurality of channel-wise analysis outputs. The second level of machine learning submodules may be configured to analyze the plurality of received channel-wise analysis outputs of the signal modality to provide an analysis output descriptive of the modality. A third level of machine learning submodules of the hierarchically arranged machine learning submodels may receive the analysis output descriptive of the modality. The third level of machine learning submodules is configured to analyze the output received from the second submodule to produce an output descriptive of a clinical interpretation of the received patient data.

In some examples, a neuromonitoring data analysis apparatus is configured to receive patient data comprising: data that are descriptive of a plurality of physical stimuli applied to a mammalian subject for responsively generating a plurality of corresponding stimuli signals in at least two neural structures of the subject's nervous system; and sensor data descriptive of a plurality of neurophysiological response signals generated in response the plurality of applied physical stimuli; determining whether or not the response signals are indicative of an anomalous characteristic with respect to at least one of the at least two neural structures; distinguish between at least one anomalous characteristic that is indicative of injury of at least one of the at least two neural structures and at least one anomalous characteristic that is not indicative of injury and/or insult of the at least one neural structure; and, optionally, providing an output in the event that the detected anomalous characteristic is indicative of injury of the at least one neural structure.

In some examples, a neuromonitoring data analysis apparatus is configured to receive patient data comprising: data that are descriptive of a plurality of physical stimuli applied to a mammalian subject for responsively generating a plurality of corresponding stimuli signals in at least two neural structures of the subject's nervous system; and sensor data descriptive of a plurality of neurophysiological response signals generated in response the plurality of applied physical stimuli; classifying a detected anomaly with respect to the response signals into one of the following categories: a first anomaly that is indicative of injury of at least one of the at least two neural structures; and a second anomaly unrelated to injury of the at least one neural structure; and, optionally, providing an output in the event that the anomaly is classified as a first anomaly. In some examples, the classifying also takes into a consideration a baseline signal associated with each one of the at least two neural structures.

In some examples, the classifying is preceded by the following steps: analyzing the received data of the applied physical stimuli and the generated response signals; and detecting, based on the analyzing, an anomaly in at least one of the generated response signals.

In some examples, the analyzing includes collectively analyzing the generated response signals and, optionally, the received data of the applied physical stimuli. In some examples, the analyzing includes collectively analyzing the received data of the applied physical stimuli, the generated response signals and the corresponding baseline signals.

In some examples, a neuromonitoring data analysis method comprises: subjecting a mammal to neural stimuli; analyzing data descriptive of signals generated in response to the applied neural stimuli; detecting an anomaly relating to the generated response signals; determining whether the detected anomaly is indicative of injury of at least one of the at least two neural structures, or not; and, optionally, providing an output in the event that the detected anomaly is indicative of injury of the at least one neural structure. In some examples, the data are also descriptive of the physical stimuli applied to the mammalian subject for responsively generating the plurality or response signals in the mammalian's nervous system. In some examples, the data that are (collectively) analyzed are also descriptive of corresponding baseline response signals. In some examples, a detected anomaly indicative of injury of the at least one neural structure pertains to a functional state of the neural structure. In some examples, the determining includes classifying a functional state of a neural structure. In some examples, the method includes classifying the neural functional state into one of the following: "NORMAL", "DROP" or "DISAPPEAR".

In some examples, the method includes (e.g., collectively) analyzing signals of a plurality of channels pertaining to a signal modality to produce a plurality of respective channel-wise analysis outputs by a first level of machine learning submodels of the hierarchically arranged learning submodels.

In some examples, the method includes receiving the plurality of channel-wise analysis outputs by a second level of machine learning submodules of the hierarchically arranged submodules, and analyzing by the second level of machine-learning submodules the plurality of received channel-wise analysis outputs of the signal modality to provide an analysis output descriptive of the modality. In some examples, method includes receiving, at a third level of machine learning submodules of the hierarchically arranged machine learning submodules, the analysis output descriptive of the modality; and analyzing, by the third level of machine learning submodules, the output received from the second level of submodules to produce an output descriptive of a clinical interpretation of the received patient data.

In some examples, by taking into consideration the plurality of neurophysiological response signals generated in the at least two neural structures and, optionally, the data descriptive of the applied physical stimuli, a false-positive rate of anomalous events identified as relating to injury of a neural structure is reduced, compared to a false-positive rate obtained if each response signal was analyzed individually.

In some examples, by taking into consideration the plurality of neurophysiological response signals generated in the at least two neural structures, and, optionally, data descriptive of the applied physical stimuli a false-negative rate of anomalous events identified as relating to injury of a neural structure is reduced, compared to a false-negative rate obtained if each response signal was analyzed individually.

The methods described herein and illustrated in the accompanying diagrams shall not be construed in a limiting manner. For example, methods described herein may include additional or even fewer processes or operations in comparison to what is described herein and/or illustrated in the diagrams. In addition, method steps are not necessarily limited to the chronological order as illustrated and described herein.

Any digital computer system, apparatus, unit, device, module and/or engine exemplified herein can be configured or otherwise programmed to implement a method disclosed herein, and to the extent that the system, apparatus, module and/or engine is configured to implement such a method, it is within the scope and spirit of the disclosure. Once the system, apparatus, module and/or engine are programmed to perform particular functions pursuant to computer readable and executable instructions from program software that implements a method disclosed herein, it in effect becomes a special purpose computer particular to embodiments of the method disclosed herein. The methods and/or processes disclosed herein may be implemented as a computer program product that may be tangibly embodied in an information carrier including, for example, in a non-transitory tangible computer-readable and/or non-transitory tangible machine-readable storage device. The computer program product may directly loadable into an internal memory of a digital computer, comprising software code portions for performing the methods and/or processes as disclosed herein.

The methods and/or processes disclosed herein may be implemented as a computer program that may be intangibly embodied by a computer readable signal medium. A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a non-transitory computer or machine-readable storage device and that can communicate, propagate, or transport a program for use by or in connection with apparatuses, systems, platforms, methods, operations and/or processes discussed herein.

The terms "non-transitory computer-readable storage device" and "non-transitory machine-readable storage device" encompasses distribution media, intermediate storage media, execution memory of a computer, and any other medium or device capable of storing for later reading by a computer program implementing embodiments of a method disclosed herein. A computer program product can be deployed to be executed on one computer or on multiple computers at one site or distributed across multiple sites and interconnected by one or more communication networks.

These computer readable and executable instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable and executable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable and executable instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The term "engine" may comprise one or more computer modules, wherein a module may be a self-contained hardware and/or software component that interfaces with a larger system. A module may comprise a machine or machines executable instructions. A module may be embodied by a circuit or a controller programmed to cause the systems, apparatuses and/or platforms to implement the method, process and/or operation as disclosed herein. For example, a module may be implemented as a hardware circuit comprising, e.g., custom VLSI circuits or gate arrays, an Application-Specific Integrated Circuit (ASIC), off-the-shelf semiconductors such as logic chips, transistors, and/or other discrete components. A module may also be implemented in programmable hardware devices such as field programmable gate arrays, programmable array logic, programmable logic devices and/or the like.

In the discussion, unless otherwise stated, adjectives such as "substantially" and "about" that modify a condition or relationship characteristic of a feature or features of an embodiment of the invention, are to be understood to mean that the condition or characteristic is defined to within tolerances that are acceptable for operation of the embodiment for an application for which it is intended.

Unless otherwise specified, the terms "substantially", "about" and/or "close" with respect to a magnitude or a numerical value may imply to be within an inclusive range of −10% to +10% of the respective magnitude or value.

"Coupled with" can mean indirectly or directly "coupled with".

It is important to note that the method may include is not limited to those diagrams or to the corresponding descriptions. For example, the method may include additional or even fewer processes or operations in comparison to what is described in the figures. In addition, embodiments of the method are not necessarily limited to the chronological order as illustrated and described herein.

Discussions herein utilizing terms such as, for example, "processing", "computing", "calculating", "determining", "establishing", "analyzing", "checking", "estimating", "deriving", "selecting", "inferring" or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes. The term determining may, where applicable, also refer to "heuristically determining".

It should be noted that where an embodiment refers to a condition of "above a threshold", this should not be construed as excluding an embodiment referring to a condition of "equal or above a threshold". Analogously, where an embodiment refers to a condition "below a threshold", this should not be construed as excluding an embodiment referring to a condition "equal or below a threshold". It is clear that should a condition be interpreted as being fulfilled if the value of a given parameter is above a threshold, then the same condition is considered as not being fulfilled if the value of the given parameter is equal or below the given threshold. Conversely, should a condition be interpreted as being fulfilled if the value of a given parameter is equal or above a threshold, then the same condition is considered as not being fulfilled if the value of the given parameter is below (and only below) the given threshold.

It should be understood that where the claims or specification refer to "a" or "an" element and/or feature, such reference is not to be construed as there being only one of that element. Hence, reference to "an element" or "at least one element" for instance may also encompass "one or more elements".

Terms used in the singular shall also include the plural, except where expressly otherwise stated or where the context otherwise requires.

In the description and claims of the present application, each of the verbs, "comprise" "include" and "have", and conjugates thereof, are used to indicate that the data portion or data portions of the verb are not necessarily a complete listing of components, elements or parts of the subject or subjects of the verb.

Unless otherwise stated, the use of the expression "and/or" between the last two members of a list of options for selection indicates that a selection of one or more of the listed options is appropriate and may be made. Further, the use of the expression "and/or" may be used interchangeably with the expressions "at least one of the following", "any one of the following" or "one or more of the following", followed by a listing of the various options.

As used herein, the phrase "A, B, C, or any combination of the aforesaid" should be interpreted as meaning all of the following: (i) A or B or C or any combination of A, B, and C, (ii) at least one of A, B, and C; (iii) A, and/or B and/or C, and (iv) A, B and/or C. Where appropriate, the phrase A, B and/or C can be interpreted as meaning A, B or C. The phrase A, B or C should be interpreted as meaning "selected from the group consisting of A, B and C". This concept is illustrated for three elements (i.e., A, B, C), but extends to fewer and greater numbers of elements (e.g., A, B, C, D, etc.).

It is appreciated that certain features of the invention, which are, for clarity, described in the context of separate embodiments or example, may also be provided in combination in a single embodiment. Conversely, various features of the invention, which are, for brevity, described in the context of a single embodiment, example and/or option, may also be provided separately or in any suitable sub-combination or as suitable in any other described embodiment, example or option of the invention. Certain features described in the context of various embodiments, examples and/or optional implementation are not to be considered essential features of those embodiments, unless the embodiment, example and/or optional implementation is inoperative without those elements.

It is noted that the terms "in some embodiments", "according to some embodiments", "for example", "e.g.", "for instance" and "optionally" may herein be used interchangeably.

The number of elements shown in the Figures should by no means be construed as limiting and is for illustrative purposes only.

It is noted that the terms "operable to" can encompass the meaning of the term "modified or configured to". In other words, a machine "operable to" perform a task can in some embodiments, embrace a mere capability (e.g., "modified") to perform the function and, in some other embodiments, a machine that is actually made (e.g., "configured") to perform the function.

Throughout this application, various embodiments may be presented in and/or relate to a range format. It should be understood that the description in range format is merely for convenience and brevity and should not be construed as an inflexible limitation on the scope of the embodiments. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

While the invention has been described with respect to a limited number of embodiments, these should not be construed as limitations on the scope of the invention, but rather as exemplifications of some of the embodiments.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A neuromonitoring data analysis apparatus configured to monitor a nervous system of a subject, the apparatus comprising a processor executing a machine learning model having a plurality of levels of hierarchically arranged machine learning sub-models configured for:

(a) analyzing each of a plurality of neurophysiological signals generated by at least two channels associated with at least one neural structure in response to application of a plurality of physical stimuli to the subject;

(b) identifying at least one neurophysiological response signal of said plurality of neurophysiological response signals indicative of injury in said at least one neural structure.

2. The apparatus of claim 1, wherein said at least two channels are associated with at least two neural structures.

3. The apparatus of claim 1, wherein said plurality of neurophysiological response signals are generated in response to simultaneous application of physical stimuli.

4. The apparatus of claim 1, wherein (b) includes distinguishing between a first anomalous event relating to injury of said at least one neural structure and a second anomalous event not relating to injury of at least one neural structure.

5. The apparatus of claim 4, wherein said second anomalous event relates to a systemic factor.

6. The apparatus of claim 5, wherein said systemic factor includes at least one from the group consisting of patient anesthesia, blood pressure, patient position and patient posture.

7. The apparatus of claim 1, wherein (b) includes comparing said plurality of neurophysiological response signals against corresponding baseline signals.

8. The apparatus of claim 1, wherein said processor is further configured for analyzing patient data including at least one from the group consisting of demographic data, anesthesia data, physiological data, surgical data, baseline motor evoked potential signal data, baseline EMG signal data, baseline EEG signal data, baseline somatosensory evoked potential signal data and reflex data.

9. The apparatus of claim 1, wherein a first level of said machine learning model is configured to associate each of said plurality of neurophysiological response signals to a specific signal modality and produce a plurality of signal modality outputs distinguishing between normal and abnormal activity.

10. The apparatus of claim 9, wherein a second level of said machine learning model is configured to analyze each signal modality output to provide an analysis output descriptive of said signal modality.

11. The apparatus of claim 10, wherein said second level is further configured to detect an occurrence of patterns of changes in aggregated signals of each signal modality.

12. The apparatus of claim 10, wherein a third level of said machine learning model interprets said analysis output as a clinical interpretation of each of said plurality of neurophysiological response signals.

13. The apparatus of claim 9, wherein each of said plurality of neurophysiological response signals is processed for feature extraction indicative of said specific signal modality.

14. The apparatus of claim 13, wherein said feature is of an MEP signal, an SSEP signal.

15. The apparatus of claim 1, wherein said processor configured for analyzing at least one non-stimulated neurophysiological signal.

16. The apparatus of claim 15, wherein said at least one non-stimulated neurophysiological signal is an EEG signal or an EMG signal.

17. The apparatus of claim 1, wherein (a) also takes into consideration data descriptive of said plurality of physical stimuli.

* * * * *